United States Patent
Hacohen et al.

(10) Patent No.: US 10,835,377 B2
(45) Date of Patent: *Nov. 17, 2020

(54) ROLLED PROSTHETIC VALVE SUPPORT

(71) Applicant: CARDIOVALVE LTD., Or Yehuda (IL)

(72) Inventors: Gil Hacohen, Ramot HaShavim (IL); Eran Miller, Moshav Beit Elazari (IL); Tal Reich, Moshav Moledet (IL); Yuval Zipory, Modi'in (IL); Rotem Neeman, Yeshuv Nirit (IL); Natalia Kruglova, Tel Aviv (IL)

(73) Assignee: CARDIOVALVE LTD., Or Yehuda (IL)

( * ) Notice: Subject to any disclaimer, the term of this patent is extended or adjusted under 35 U.S.C. 154(b) by 431 days.

This patent is subject to a terminal disclaimer.

(21) Appl. No.: 15/600,190

(22) Filed: May 19, 2017

(65) Prior Publication Data
US 2017/0252159 A1 Sep. 7, 2017

Related U.S. Application Data

(63) Continuation of application No. 14/161,921, filed on Jan. 23, 2014, now Pat. No. 9,681,952.
(Continued)

(51) Int. Cl.
*A61F 2/24* (2006.01)

(52) U.S. Cl.
CPC .......... *A61F 2/2427* (2013.01); *A61F 2/2409* (2013.01); *A61F 2/2418* (2013.01);
(Continued)

(58) Field of Classification Search
CPC ........ A61F 2/24; A61F 2/2409; A61F 2/2418; A61F 2/2427; A61F 2/2436;
(Continued)

(56) References Cited

U.S. PATENT DOCUMENTS

| 4,261,342 A | 4/1981 | Aranguren Duo |
| 4,423,525 A | 1/1984 | Vallana et al. |

(Continued)

FOREIGN PATENT DOCUMENTS

| EP | 1264582 A2 | 12/2002 |
| EP | 1768630 B1 | 7/2015 |

(Continued)

OTHER PUBLICATIONS

An International Search Report and a Written Opinion both dated May 13, 2019, which issued during the prosecution of Applicant's PCT/IL2018/051350.

(Continued)

*Primary Examiner* — Julie A Szpira
(74) *Attorney, Agent, or Firm* — Sughrue Mion, PLLC

(57) ABSTRACT

Apparatus is provided for use at a native valve of a heart of a subject. The apparatus includes a delivery tube, transluminally advanceable to the heart; and a prosthetic valve support, configured to support a prosthetic valve at the native valve, and comprising an upstream support portion. The upstream support portion has a working configuration in which it is generally annular and has (1) a tissue-contacting side configured to be placed against an atrial surface of the native valve, and (2) an opposing side, and defines an opening therebetween. The upstream support portion also has a delivery configuration in which the upstream support portion is rolled up to define a channel, and is disposed within the delivery tube. The upstream support portion is configured to be transitioned from the delivery configuration to the working configuration by being exposed from the delivery tube, and unrolled.

9 Claims, 18 Drawing Sheets

Related U.S. Application Data

(60) Provisional application No. 61/756,034, filed on Jan. 24, 2013, provisional application No. 61/756,049, filed on Jan. 24, 2013.

(52) U.S. Cl.
CPC .... *A61F 2/2436* (2013.01); *A61F 2220/0016* (2013.01); *A61F 2220/0025* (2013.01); *A61F 2220/0075* (2013.01); *A61F 2250/0098* (2013.01)

(58) Field of Classification Search
CPC .................. A61F 2/2442; A61F 2/2445; A61F 2220/0016; A61F 2220/0025; A61F 2220/0075; A61F 2250/0098
See application file for complete search history.

(56) References Cited

U.S. PATENT DOCUMENTS

| | | |
|---|---|---|
| 4,853,986 A | 8/1989 | Allen |
| 4,892,541 A | 1/1990 | Alonso |
| 5,108,420 A | 4/1992 | Marks |
| 5,314,473 A | 5/1994 | Godin |
| 5,405,378 A | 4/1995 | Strecker |
| 5,443,500 A | 8/1995 | Sigwart |
| 5,607,444 A | 3/1997 | Lam |
| 5,607,470 A | 3/1997 | Milo |
| 5,647,857 A | 7/1997 | Anderson et al. |
| 5,702,397 A | 12/1997 | Goble et al. |
| 5,765,682 A | 6/1998 | Bley et al. |
| 5,776,140 A | 7/1998 | Cottone |
| 5,868,777 A | 2/1999 | Lam |
| 5,873,906 A | 2/1999 | Lau et al. |
| 5,954,766 A | 9/1999 | Zadno-Azizi et al. |
| 5,957,949 A * | 9/1999 | Leonhardt .................. A61F 2/07 606/108 |
| 5,980,565 A | 11/1999 | Jayaraman |
| 6,010,530 A | 1/2000 | Goicoechea |
| 6,019,787 A | 2/2000 | Richard et al. |
| 6,042,607 A | 3/2000 | Williamson, IV et al. |
| 6,074,417 A | 6/2000 | Peredo |
| 6,120,534 A | 9/2000 | Ruiz |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vazquez et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,402,780 B2 | 6/2002 | Williamson, IV et al. |
| 6,419,696 B1 | 7/2002 | Ortiz et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,582,464 B2 * | 6/2003 | Gabbay .................. A61F 2/2412 623/2.38 |
| 6,652,556 B1 | 11/2003 | VanTassel et al. |
| 6,669,724 B2 | 12/2003 | Park et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,733,525 B2 | 5/2004 | Yang et al. |
| 6,764,514 B1 * | 7/2004 | Li ........................... A61F 2/441 623/17.12 |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,951,571 B1 | 10/2005 | Srivastava |
| 6,960,217 B2 | 11/2005 | Bolduc |
| 6,964,684 B2 | 11/2005 | Ortiz et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,336 B2 | 9/2006 | Artof et al. |
| 7,101,395 B2 | 9/2006 | Tremulis et al. |
| 7,137,184 B2 | 11/2006 | Schreck |
| 7,172,625 B2 | 2/2007 | Shu et al. |
| 7,198,646 B2 | 4/2007 | Figulla et al. |
| 7,201,772 B2 | 4/2007 | Schwammenthal et al. |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,571 B2 | 5/2008 | Pease et al. |
| 7,374,573 B2 | 5/2008 | Gabbay |
| 7,377,938 B2 | 5/2008 | Sarac et al. |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lasninski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,527,646 B2 | 5/2009 | Rahdert et al. |
| 7,582,111 B2 | 9/2009 | Krolik et al. |
| 7,585,321 B2 | 9/2009 | Cribier |
| 7,625,403 B2 | 12/2009 | Krivoruchko |
| 7,632,302 B2 | 12/2009 | Vreeman et al. |
| 7,648,528 B2 | 1/2010 | Styrc |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,799,069 B2 | 9/2010 | Bailey et al. |
| 7,803,181 B2 | 9/2010 | Furst et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,672 B2 | 6/2011 | Salahieh et al. |
| 7,967,833 B2 | 6/2011 | Sterman et al. |
| 7,967,857 B2 | 6/2011 | Lane |

(56) References Cited

U.S. PATENT DOCUMENTS

| | | |
|---|---|---|
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak et al. |
| 8,021,420 B2 | 9/2011 | Dolan |
| 8,021,421 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sullivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde et al. |
| 8,075,611 B2 | 12/2011 | Millwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahleh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chaleklan et al. |
| 8,287,591 B2 | 10/2012 | Keidar et al. |
| 8,298,280 B2 | 10/2012 | Yadin et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,474,460 B2 | 7/2013 | Barrett et al. |
| 8,500,821 B2 | 8/2013 | Sobrino-Serrano et al. |
| 8,529,431 B2 * | 9/2013 | Baker .............. A61B 17/00234 600/37 |
| 8,545,544 B2 | 10/2013 | Spenser et al. |
| 8,551,161 B2 | 10/2013 | Dgian |
| 8,562,672 B2 | 10/2013 | Bonhoeffer et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray, III et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,657,672 B2 | 2/2014 | Sequin |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,840,684 B2 | 9/2014 | Karapetian et al. |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,373 B2 | 3/2015 | Chau et al. |
| 8,986,375 B2 | 3/2015 | Garde et al. |
| 8,992,608 B2 | 3/2015 | Haug et al. |
| 8,998,982 B2 | 4/2015 | Richter et al. |
| 9,005,273 B2 | 4/2015 | Salahieh et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich, Jr. et al. |

(56) References Cited

U.S. PATENT DOCUMENTS

| | | |
|---|---|---|
| 9,072,603 B2 | 7/2015 | Tuval et al. |
| 9,084,676 B2 | 7/2015 | Chau et al. |
| 9,095,434 B2 | 8/2015 | Rowe |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,138,312 B2 | 9/2015 | Tuval et al. |
| 9,173,738 B2 | 11/2015 | Murray, III et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman, III et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweih, Jr. et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amlplatz et al. |
| 9,763,657 B2 | 9/2017 | Hacohen et al. |
| 9,763,817 B2 | 9/2017 | Roeder |
| D800,908 S | 10/2017 | Hariton et al. |
| 9,788,941 B2 | 10/2017 | Hacohen |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,206,668 B2 * | 2/2019 | McGoldrick .......... B05D 1/007 |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,327,895 B2 | 6/2019 | Lozonschi et al. |
| 10,376,361 B2 | 8/2019 | Gross et al. |
| 10,456,256 B2 * | 10/2019 | Braido ................. A61F 2/2442 |
| 10,531,872 B2 | 1/2020 | Hacohen et al. |
| 10,548,731 B2 | 2/2020 | Lashinski et al. |
| 2001/0002445 A1 | 5/2001 | Vesely |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0009236 A1 | 1/2003 | Godin |
| 2003/0036791 A1 | 2/2003 | Philipp et al. |
| 2003/0060846 A1 * | 3/2003 | Egnelov ............. A61B 17/0057 |
| | | 606/213 |
| 2003/0060875 A1 | 3/2003 | Wittens |
| 2003/0069635 A1 | 4/2003 | Cartledge et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavenik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright, Jr. et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay et al. |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0047297 A1 | 3/2006 | Case |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Hebert et al. |
| 2006/0135964 A1 | 6/2006 | Vesely |
| 2006/0155357 A1 | 7/2006 | Melsheimer |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |

(56) References Cited

U.S. PATENT DOCUMENTS

| | | |
|---|---|---|
| 2007/0027549 A1 | 2/2007 | Godin |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Kriveruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidiund et al. |
| 2008/0200980 A1* | 8/2008 | Robin ............... A61F 2/2418 623/2.11 |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0171363 A1 | 7/2009 | Chevron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0299449 A1 | 12/2009 | Styrc |
| 2009/0306768 A1 | 12/2009 | Quadri |
| 2009/0319037 A1 | 12/2009 | Rowe et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0230603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0021985 A1 | 1/2011 | Spargias |
| 2011/0022165 A1 | 1/2011 | Oba et al. |
| 2011/0029067 A1* | 2/2011 | McGuckin, Jr. ............ A61F 2/82 623/1.24 |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fenster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137397 A1* | 6/2011 | Chau ............... A61F 2/2412 623/1.11 |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Mein et al. |

(56) References Cited

U.S. PATENT DOCUMENTS

| | | |
|---|---|---|
| 2011/0224785 A1 | 9/2011 | Hacohen |
| 2011/0238094 A1* | 9/2011 | Thomas ............... A61F 2/0063 606/151 |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao et al. |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1* | 3/2012 | Bolling ............... A61F 2/2445 623/2.11 |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Meisheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0300063 A1 | 11/2012 | Majkrzak et al. |
| 2012/0310328 A1* | 12/2012 | Olson ............... A61F 2/07 623/1.26 |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150915 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0331929 A1 | 12/2013 | Mitre et al. |
| 2014/0000112 A1 | 1/2014 | Braido et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1* | 7/2014 | Vidlund ............... A61F 2/2418 623/2.14 |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |

(56) References Cited

U.S. PATENT DOCUMENTS

| | | |
|---|---|---|
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0350662 A1* | 11/2014 | Vaturi .................. A61F 2/2412 623/2.1 |
| 2014/0350670 A1* | 11/2014 | Keranen ............... A61F 2/2463 623/2.36 |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0106539 A1 | 4/2016 | Buchbincier et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0310268 A1 | 10/2016 | Oba et al. |
| 2016/0317301 A1 | 11/2016 | Quadri et al. |
| 2016/0317305 A1 | 11/2016 | Pelled et al. |
| 2016/0324635 A1 | 11/2016 | Vidlund et al. |
| 2016/0324640 A1 | 11/2016 | Gifford, III et al. |
| 2016/0331526 A1 | 11/2016 | Schweich, Jr. et al. |
| 2016/0331527 A1 | 11/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2017/0333187 A1 | 11/2017 | Marlton et al. |
| 2018/0021129 A1 | 1/2018 | Peterson et al. |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0153689 A1 | 6/2018 | Maimon et al. |
| 2018/0177594 A1 | 6/2018 | Patel et al. |
| 2018/0206983 A1 | 7/2018 | Noe et al. |
| 2018/0250126 A1 | 9/2018 | O'connor et al. |
| 2018/0296336 A1 | 10/2018 | Cooper et al. |
| 2018/0296341 A1 | 10/2018 | Noe et al. |
| 2018/0344457 A1 | 12/2018 | Gross et al. |
| 2018/0353294 A1 | 12/2018 | Calomeni et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0117391 A1 | 4/2019 | Humair |
| 2019/0175339 A1 | 6/2019 | Vidlund |
| 2019/0216602 A1 | 7/2019 | Lozonschi |
| 2019/0350701 A1 | 11/2019 | Adamek-bowers et al. |
| 2019/0388218 A1 | 12/2019 | Vidlund et al. |
| 2019/0388220 A1 | 12/2019 | Vidlund et al. |

FOREIGN PATENT DOCUMENTS

| | | |
|---|---|---|
| WO | 98/43557 A1 | 10/1998 |
| WO | 99/30647 A1 | 6/1999 |
| WO | 00/47139 A1 | 8/2000 |
| WO | 01/62189 A1 | 8/2001 |
| WO | 01/87190 A2 | 11/2001 |
| WO | 2005/107650 A2 | 11/2005 |
| WO | 2006/007401 A2 | 1/2006 |
| WO | 2006/054930 A1 | 5/2006 |
| WO | 2006/070372 A2 | 7/2006 |
| WO | 2006/089236 A1 | 8/2006 |
| WO | 2007/059252 A1 | 5/2007 |
| WO | 2008/013915 A3 | 1/2008 |
| WO | 2008/029296 A2 | 3/2008 |
| WO | 2008/070797 A2 | 6/2008 |
| WO | 200//103722 A2 | 8/2008 |
| WO | 2009/033469 A1 | 3/2009 |
| WO | 2009/053497 A1 | 4/2009 |
| WO | 2009/091509 A1 | 7/2009 |
| WO | 2010/006627 A1 | 1/2010 |
| WO | 2010/037141 A1 | 4/2010 |
| WO | 2010/057262 A1 | 5/2010 |
| WO | 2010/081033 A1 | 7/2010 |
| WO | 2010/121076 A2 | 10/2010 |
| WO | 2011/025972 A2 | 3/2011 |
| WO | 2011/069048 A2 | 6/2011 |
| WO | 2011/106137 A1 | 9/2011 |
| WO | 2011/111047 A2 | 9/2011 |
| WO | 2011/137531 A1 | 11/2011 |
| WO | 2011/143263 A2 | 11/2011 |
| WO | 2012/011108 A2 | 1/2012 |
| WO | 2012/024428 A2 | 2/2012 |
| WO | 2012/036740 A2 | 3/2012 |
| WO | 2012/048035 A2 | 4/2012 |
| WO | 2012/127309 A1 | 9/2012 |
| WO | 2012/177942 A2 | 12/2012 |
| WO | 2013/021374 A2 | 2/2013 |
| WO | 2013/021375 A2 | 2/2013 |
| WO | 2013/059747 A1 | 4/2013 |
| WO | 2013/072496 | 5/2013 |
| WO | 2013/078497 A1 | 6/2013 |
| WO | 2013/128436 A1 | 9/2013 |
| WO | 2013/175468 | 11/2013 |
| WO | 2014/022124 A1 | 2/2014 |
| WO | 2014/145338 A1 | 9/2014 |
| WO | 2014/164364 A1 | 10/2014 |
| WO | 2014/194178 A1 | 12/2014 |
| WO | 2015/173794 A1 | 11/2015 |
| WO | 2016/093877 A1 | 6/2016 |
| WO | 2017/223486 A1 | 12/2017 |
| WO | 2018/025260 A1 | 2/2018 |
| WO | 2018/029680 A1 | 2/2018 |
| WO | 2018039631 A1 | 3/2018 |
| WO | 2018/106837 A1 | 6/2018 |

(56) References Cited

FOREIGN PATENT DOCUMENTS

| WO | 2018/112429 | A1 | 6/2018 |
|---|---|---|---|
| WO | 2018/118717 | A1 | 6/2018 |
| WO | 2018/131042 | A2 | 7/2018 |
| WO | 2018/131043 | A1 | 7/2018 |
| WO | 2019/195860 | | 10/2019 |

OTHER PUBLICATIONS

An International Search Report and a Written Opinion both dated Apr. 25, 2019, which issued during the prosecution of Applicant's PCT/IL2019/050142.
An International Search Report and a Written Opinion both dated Jan. 25, 2019, which issued during the prosecution of Applicant's PCT/IL2018/051122.
An International Search Report and a Written Opinion both dated Dec. 5, 2018, which issued during the prosecution of Applicant's PCT/IL2018/050725.
An International Preliminary Report on Patentability dated Feb. 12, 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Mar. 25, 2019, which issued during the prosecution of European Patent Application No. 14710060.6.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
International Search Report and Written Opinion dated Nov. 9, 2018, PCT/IL2018/050869.
Extended European Search Report dated Sep. 26, 2018; Appln. No. 18186764.7.
The First Chinese Office Action dated Nov. 5, 2018; Appln. No. 201680008328.5.
Invitation to pay additional fees dated Oct. 11, 2018; PCT/IL2018/050725.
USPTO NFOA dated Dec. 4, 2018 in connection with U.S. Appl. No. 16/045,059.
USPTO NOA mailed Sep. 25, 2018 in connection with U.S. Appl. No. 15/188,507.
Invitation to pay additional fees dated Jan. 2, 2018; PCT/L2017/050849.
USPTO Interview Summary dated Feb. 8, 2018 in connection with U.S. Appl. No. 15/213,791.
USPTO NFOA dated Jan. 5, 2018 in connection with U.S. Appl. No. 15/541,783.
USPTO NFOA dated Feb. 2, 2018 in connection with U.S. Appl. No. 15/329,920.
USPTO NFOA dated Feb. 7, 2018 in connection with U.S. Appl. No. 15/197,069.
USPTO NFOA dated Oct. 23, 2017 in connection with U.S. Appl. No. 14/763,004.
USPTO NFOA dated Dec. 7, 2017 in connection with U.S. Appl. No. 15/213,791.
Invitation to pay Additional Fees dated Sep. 29, 2017; PCT/IL2017/050873.
Extended European Search Report dated Jun. 29, 2017; Appln. 11809374.9.
Alexander S. Geha, et al; "Replacement of Degenerated Mital and Aortic Bioprostheses Without Explantation", Ann. Thorac. Surg. Jun. 2001; 72:1509-1514.
Dominique Himbert, MD; "Mitral Regurgitation and Stenosis from Bioprosthesis and Annuloplasty Failure: Transcatheter approaches and outcomes", 24 pages, Oct. 28, 2013.
J. Jansen, et al; "Detachable shape-memory sewing ring for heart valves", Artificial Organs, 16:294-297 1992 (An Abstract).
Frank Langer MD, et al; "RING plus STRING: Papillary muscle repositioning as an adjunctive repair technique for ischemic mitral regurgitation", J. Thorac Cardiovasc. Surg. 133:247-9, Jan. 2007.
Frank Langer, MD, et al: "RING+STRING: Successful Repair Technique for Ischemic Mitral Regurgitation With Severe Leaflet lathering", Circulation 120[suppl 1]: S85-S91. Sep. 2009.
Righini presentation EuroPCR May 2015 (Saturn)-(downloaded from: https://www.pcronline.com/Cases-resourceimages/Resources/Course-videos-slides/2015/Cardiovascularinnovation-pipeline-Mitral-and-tricuspid-valve-interventions).
Saturn Project—a novel solution for transcatheter heart valve replacement specifically designed to address clinical therapeutic needs on mitral valve: Dec. 2016.
John G. Webb, et al; "Transcatheter Valve-in-Valve Implantation for Failed Bioprosthetic Heart Valves", Circulation, Apr. 2010, 121: 1848-1857.
An Office Action dated Jun. 6, 2018, which issued during the prosecution of UK Patent Application No. 1720803.4.
An Office Action dated Jun. 18, 2018, which issued during the prosecution of UK Patent Application No. 1800399.6.
An International Search Report and a Written Opinion both dated Jun. 20, 2018, which issued during the prosecution of Applicant's PCT/IL2018/050024.
USPTO AA dated Apr. 2, 2018 in connection with U.S. Appl. No. 14/763,004.
USPTO NFOA dated Apr. 20, 2018 in connection with U.S. Appl. No. 15/886,517.
USPTO NFOA dated Jun. 28, 2018 in connection with U.S. Appl. No. 29/635,658.
USPTO NFOA dated Jun. 28, 2018 in connection with U.S. Appl. No. 29/635,661.
USPTO NFOA dated Aug. 9, 2018 in connection with U.S. Appl. No. 15/899,858.
USPTO NFOA dated Aug. 9, 2018 in connection with U.S. Appl. No. 15/902,403.
USPTO NOA mailed Apr. 20, 2018 in connection with U.S. Appl. No. 15/878,206.
USPTO NFOA dated Jul. 26, 2018 in connection with U.S. Appl. No. 15/872,501.
USPTO RR dated May 4, 2018 in connection with U.S. Appl. No. 15/872,501.
An Office Action dated Nov. 1, 2019, which issued during the prosecution of U.S. Appl. No. 15/872,501.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
An Office Action dated Aug. 1, 2019, which issued during the prosecution of U.S. Appl. No. 15/668,559.
An Office Action dated Aug. 16, 2019, which issued during the prosecution of U.S. Appl. No. 15/668,659.
An Office Action dated Jun. 19, 2019, which issued during the prosecution of U.S. Appl. No. 15/682,789.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.

(56) References Cited

OTHER PUBLICATIONS

USPTO FOA dated Feb. 10, 2014 in connection with U.S. Appl. No. 13/033,852.
USPTO FOA dated Feb. 15, 2013 in connection with U.S. Appl. No. 12/840,463.
USPTO FOA dated May 23, 2014 in connection with U.S. Appl. No. 13/412,814.
USPTO FOA dated Jul. 18, 2013 in connection with U.S. Appl. No. 13/044,694.
USPTO FOA dated Jul. 23, 2013 in connection with U.S. Appl. No. 12/961,721.
USPTO NFOA dated Jan. 18, 2017 in connection with U.S. Appl. No. 14/626,267.
USPTO NFOA dated Jan. 21, 2016 in connection with U.S. Appl. No. 14/237,264.
USPTO NFOA dated Feb. 6, 2013 in connection with U.S. Appl. No. 13/412,814.
USPTO NFOA dated Feb. 7, 2017 in connection with U.S. Appl. No. 14/689,608.
USPTO NFOA dated May 29, 2012 in connection with U.S. Appl. No. 12/840,463.
USPTO NFOA dated Jun. 4, 2014 in connection with U.S. Appl. No. 12/840,463.
USPTO NFOA dated Jun. 17, 2014 in connection with U.S. Appl. No. 12/961,721.
USPTO NFOA dated Jul. 1, 2016 in connection with U.S. Appl. No. 14/161,921.
USPTO NFOA dated Jul. 2, 2014 in connection with U.S. Appl. No. 13/811,308.
USPTO NFOA dated Jul. 3, 2014 in connection with U.S. Appl. No. 13/033,852.
USPTO NFOA dated Aug. 2, 2013 in connection with U.S. Appl. No. 13/033,852.
USPTO NFOA dated Sep. 12, 2013 in connection with U.S. Appl. No. 13/412,814.
USPTO NFOA dated Sep. 19, 2014 in connection with U.S. Appl. No. 13/044,694.
USPTO NFOA dated Nov. 8, 2013 in connection with U.S. Appl. No. 12/840,463.
USPTO NFOA dated Nov. 23, 2012 in connection with U.S. Appl. No. 13/033,852.
USPTO NFOA dated Nov. 27, 2015 in connection with U.S. Appl. No. 14/626,267.
USPTO NFOA dated Nov. 28, 2012 in connection with U.S. Appl. No. 12/961,721.
USPTO NFOA dated Dec. 10, 2015 in connection with U.S. Appl. No. 14/237,258.
USPTO NFOA dated Dec. 31, 2012 in connection with U.S. Appl. No. 13/044,694.
USPTO NOA mailed Mar. 29, 2017 in connection with U.S. Appl. No. 14/161,921.
USPTO NOA mailed Aug. 15, 2014 in connection with U.S. Appl. No. 13/412,814.
USPTO RR dated Jan. 20, 2016 in connection with U.S. Appl. No. 14/161,921.
USPTO RR dated Feb. 3, 2014 in connection with U.S. Appl. No. 13/811,308.
USPTO RR dated Jul. 2, 2012 in connection with U.S. Appl. No. 13/033,852.
USPTO RR dated Aug. 13, 2012 in connection with U.S. Appl. No. 13/044,694.
USPTO RR dated Aug. 14, 2012 in connection with U.S. Appl. No. 12/961,721.
USPTO RR dated Sep. 26, 2016 in connection with U.S. Appl. No. 14/763,004.
Extended European Search Report dated Feb. 18, 2015; Appln. No. 12621522.5-1651/2739214 PCT/IL2012000293.
EPO Office Action dated Feb. 10, 2017; Appln. No. 12 821 522.5-1651.
UK Office Action dated Feb. 8, 2017; Appln. No. 1613219.3.
Invitation to Pay Additional Fees dated Jun. 12, 2014 PCT/IL2014/050087.
IPRP issued Dec. 2, 2013; PCT/IL2011/000582.
IPRP issued Sep. 11, 2012; PCT/IL2011/000231.
IPRP issued Feb. 11, 2014; PCT/IL2012/000292.
IPRP issued Feb. 11, 2014; PCT/IL2012/000293.
International Search Report and Written Opinion dated Oct. 13, 2011; PCT/IL11/000231.
International Search Report and Written Opinion dated Dec. 5, 2011; PCT/IL11/00582.
International Search Report and Written Opinion dated Feb. 6, 2013; PCT/IL12/00293.
International Search Report and Written Opinion dated Mar. 17, 2014: PCT/IL13/50937.
International Search Report and Written Opinion dated Feb. 6, 2013; PCT/IL12/00292.
International Search Report and Written Opinion dated Apr. 9, 2014; PCT/IL2014/050087.
International Search Report and Written Opinion dated Oct. 27, 2015; PCT/IL2015/050792.
International Search Report and Written Opinion dated May 30, 2016; PCT/IL2016/050125.
U.S. Appl. No. 61/283,819.
U.S. Appl. No. 61/492,449.
U.S. Appl. No. 61/515,372.
U.S. Appl. No. 61/525,281.
U.S. Appl. No. 61/537,276.
U.S. Appl. No. 61/555,160.
U.S. Appl. No. 61/588,892.
U.S. Appl. No. 61/756,034.
U.S. Appl. No. 61/756,049.
An Office Action dated Jan. 6, 2020 which issued during the prosecution of U.S. Appl. No. 16/660,231.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
Notice of Allowance dated Januar 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's Euroean App No. 16706913.7.
Notice of Allowance dated Mar. 12, 2020, which issued during the prosecution of U.S. Appl. No. 16/460,313.
An Office Action dated Feb. 6, 2020, which issued during the prosecution of U.S. Appl. No. 15/668,659.
An Office Action dated Jan. 3, 2020, which issued during the prosecution of U.S. Appl. No. 16/678,355.

\* cited by examiner

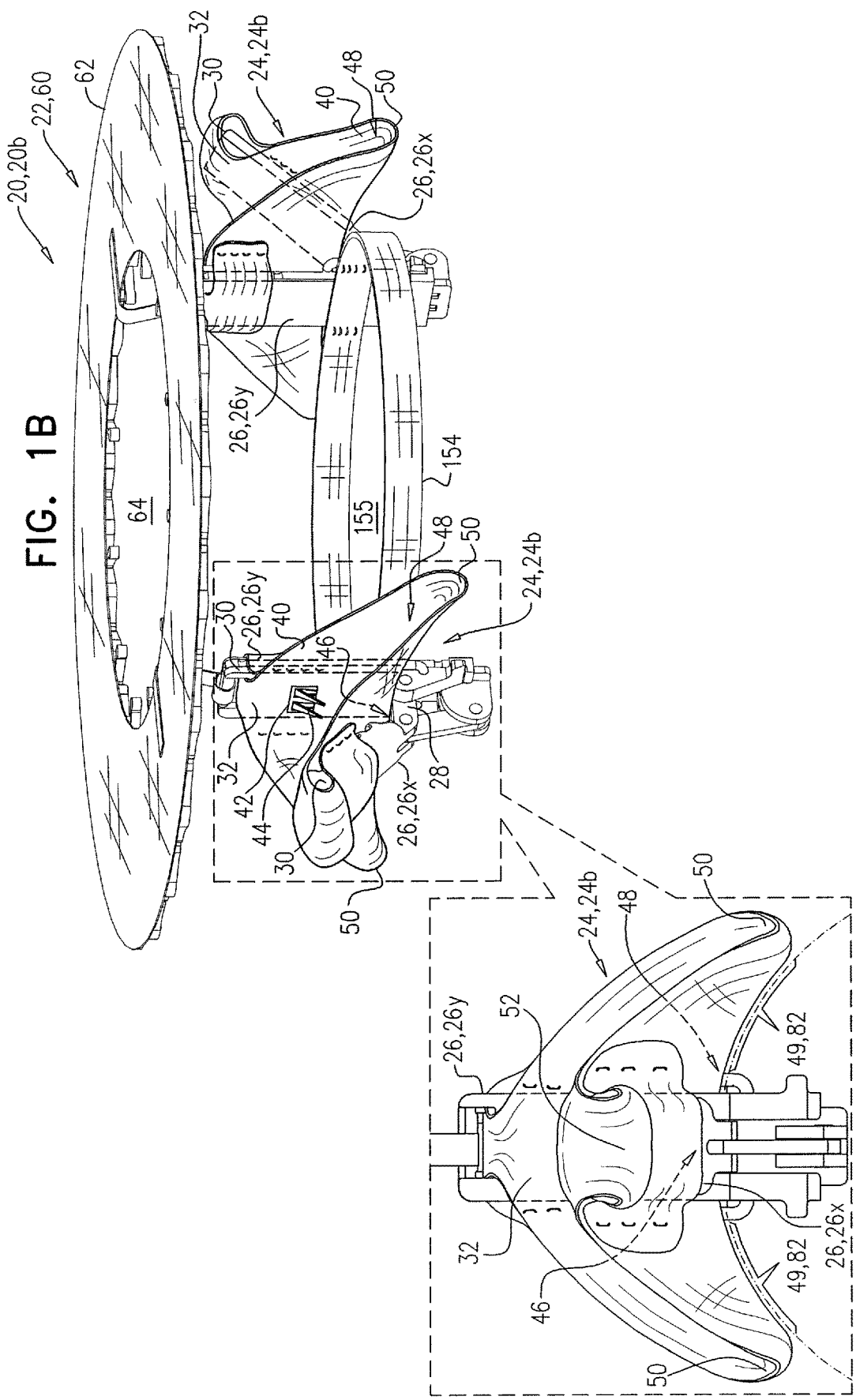

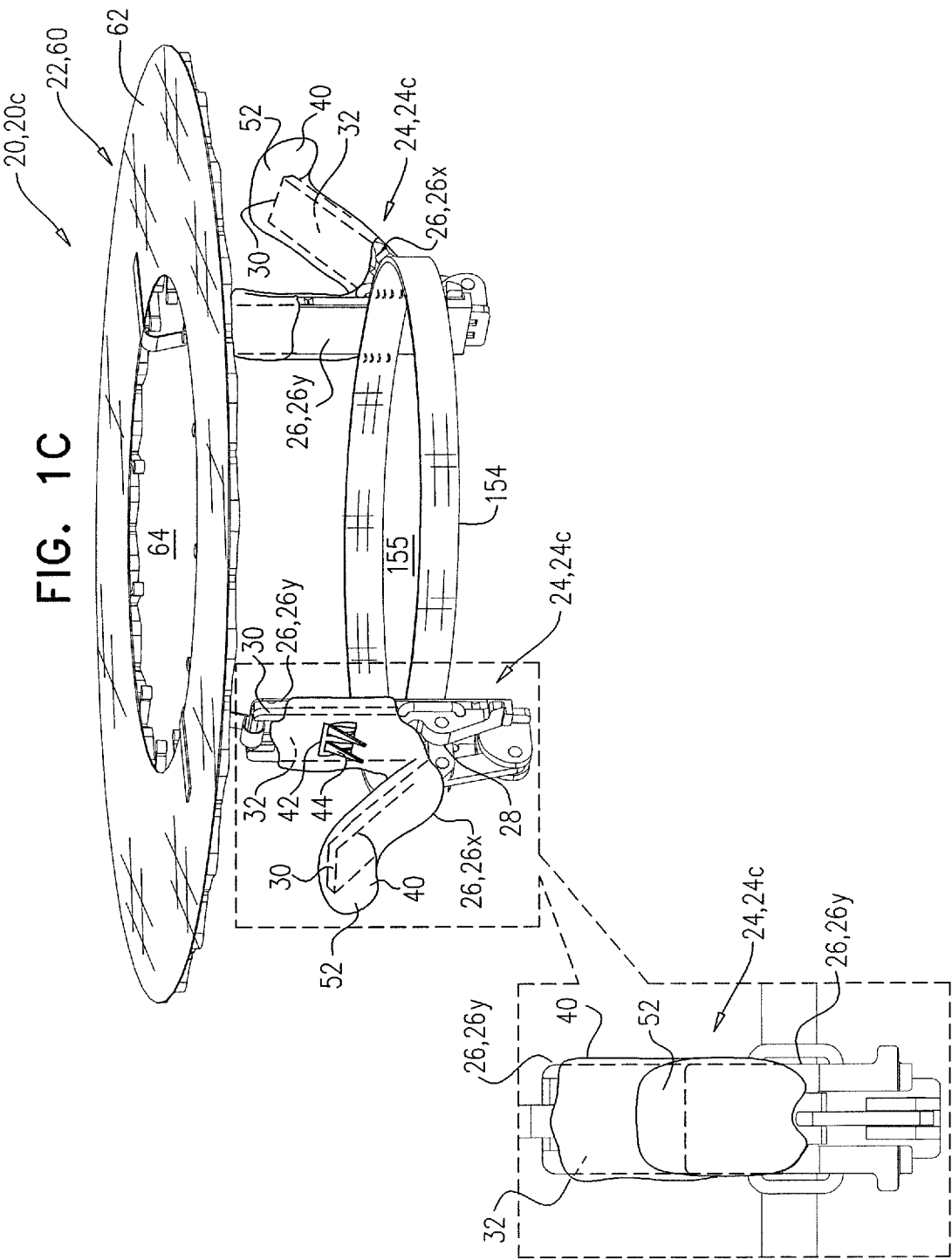

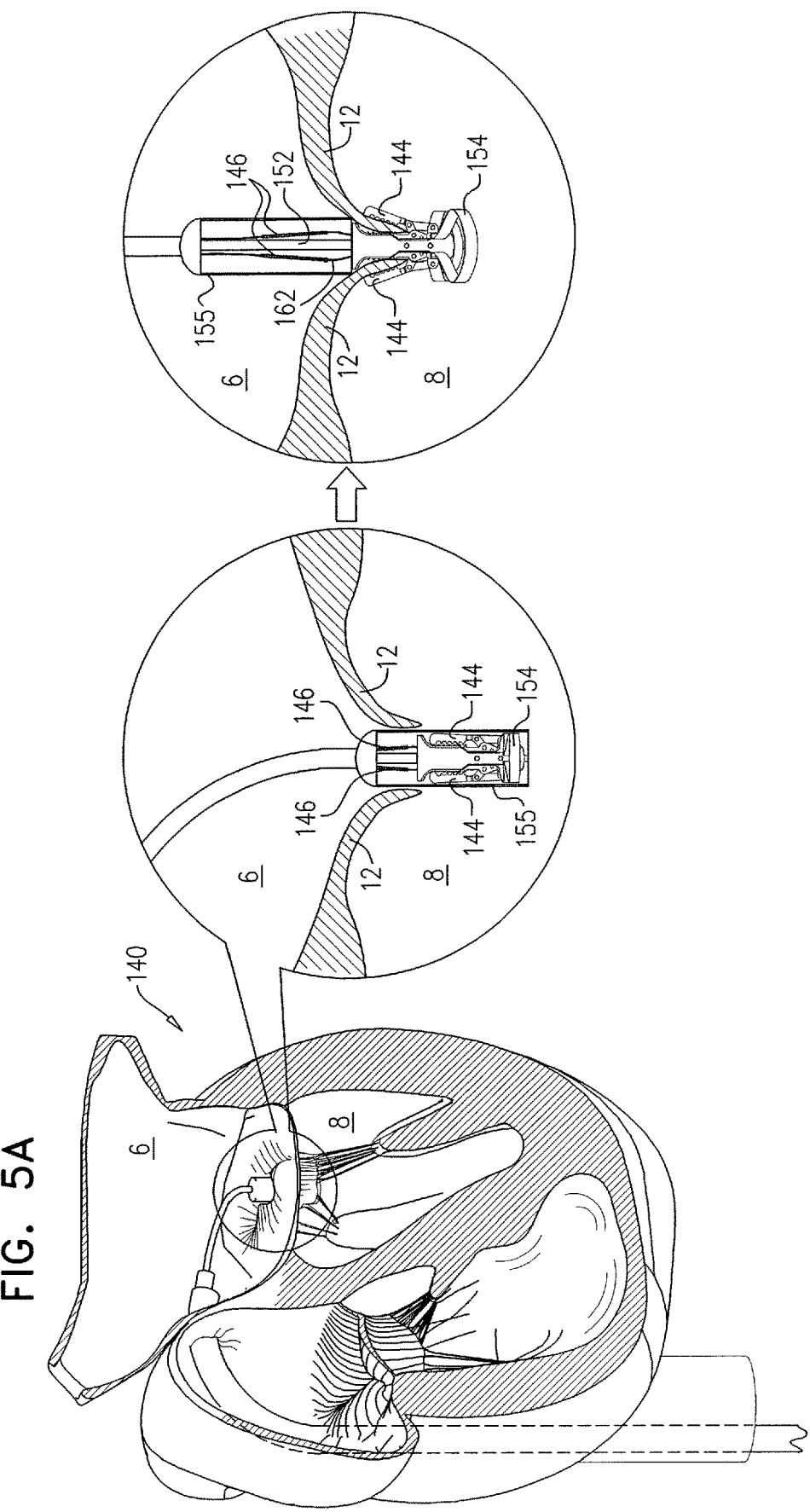

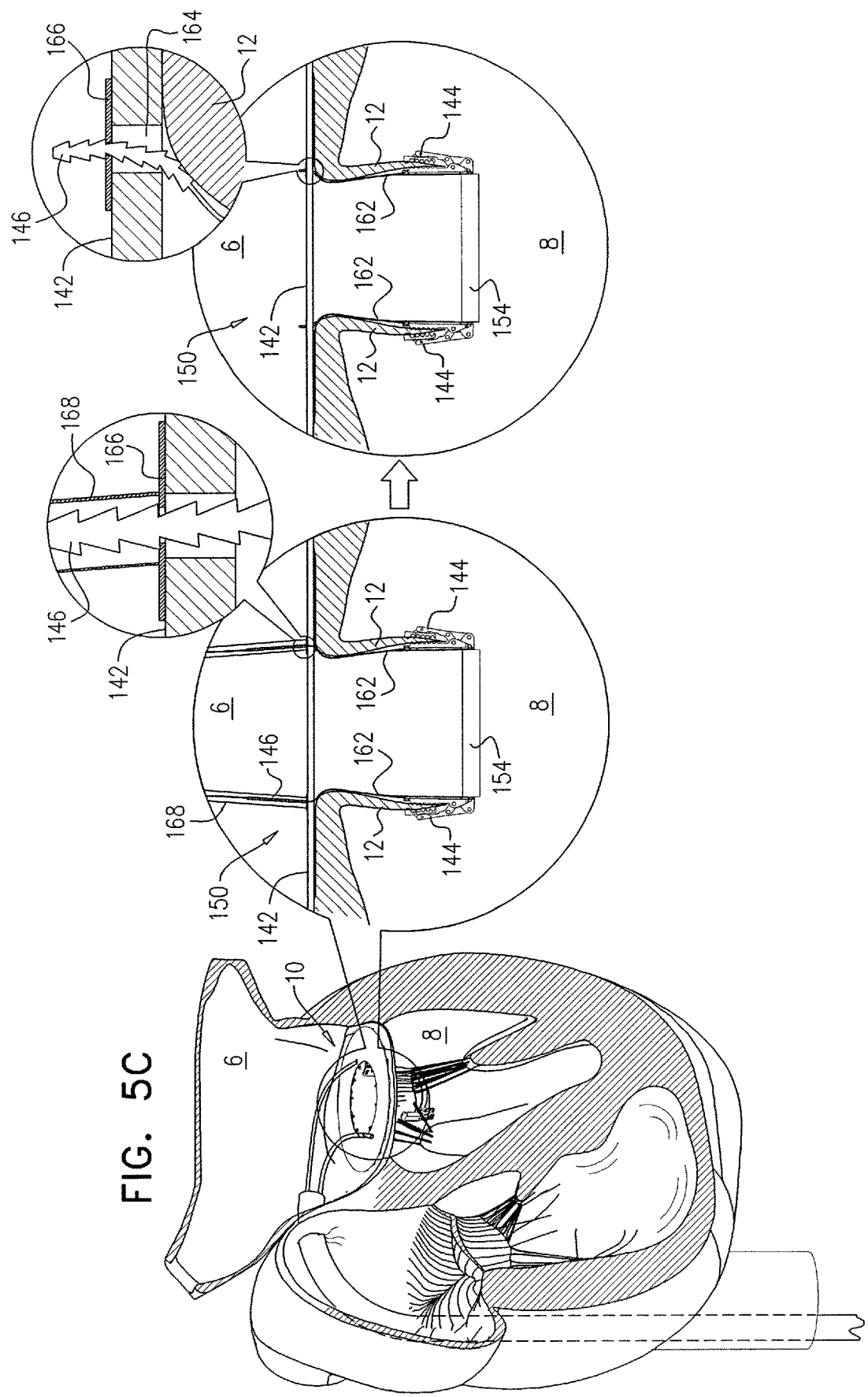

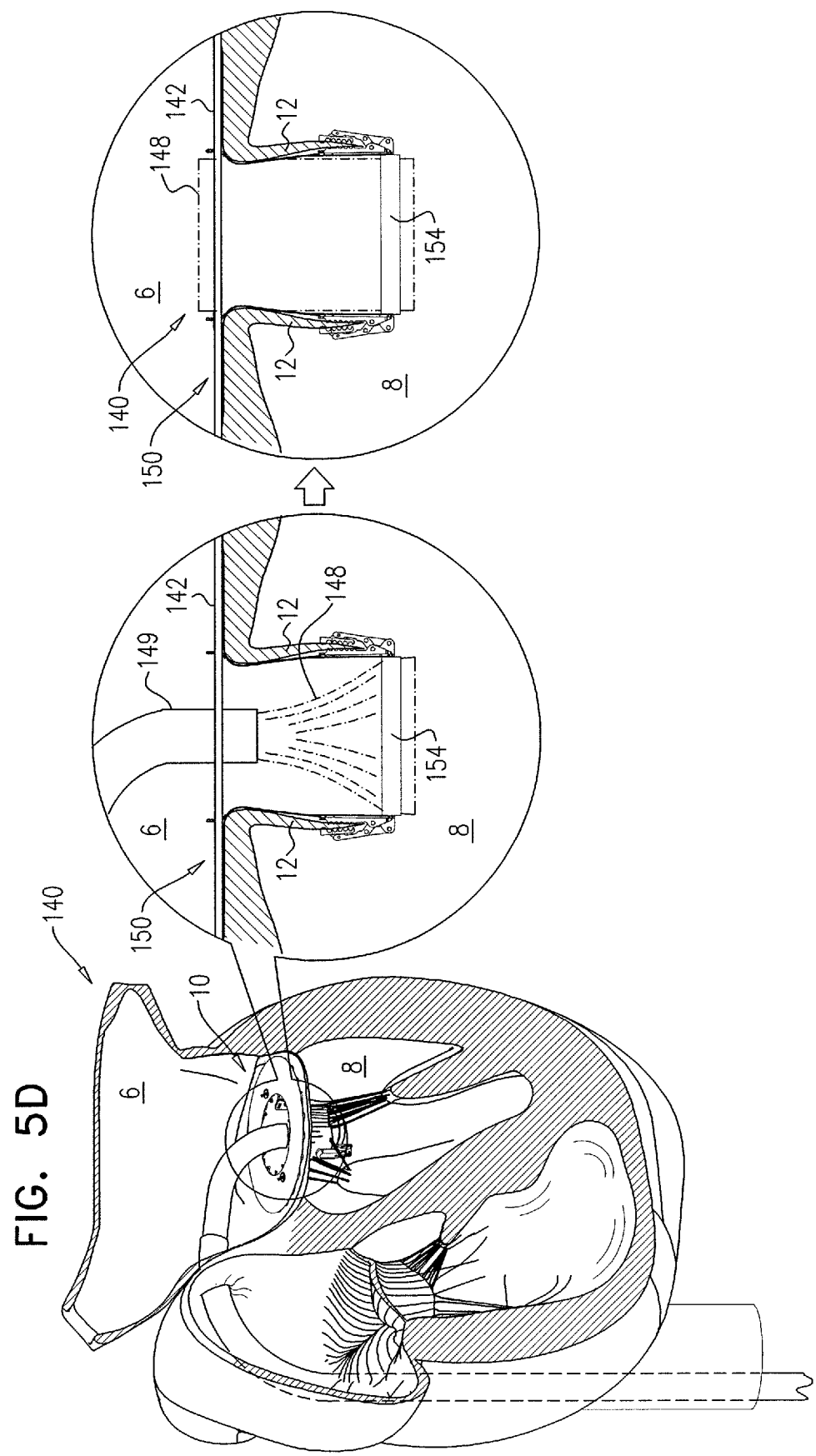

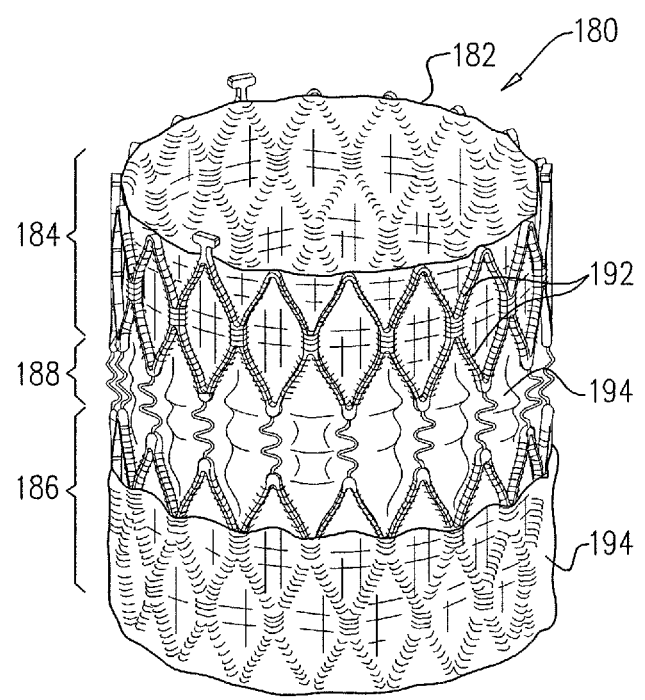

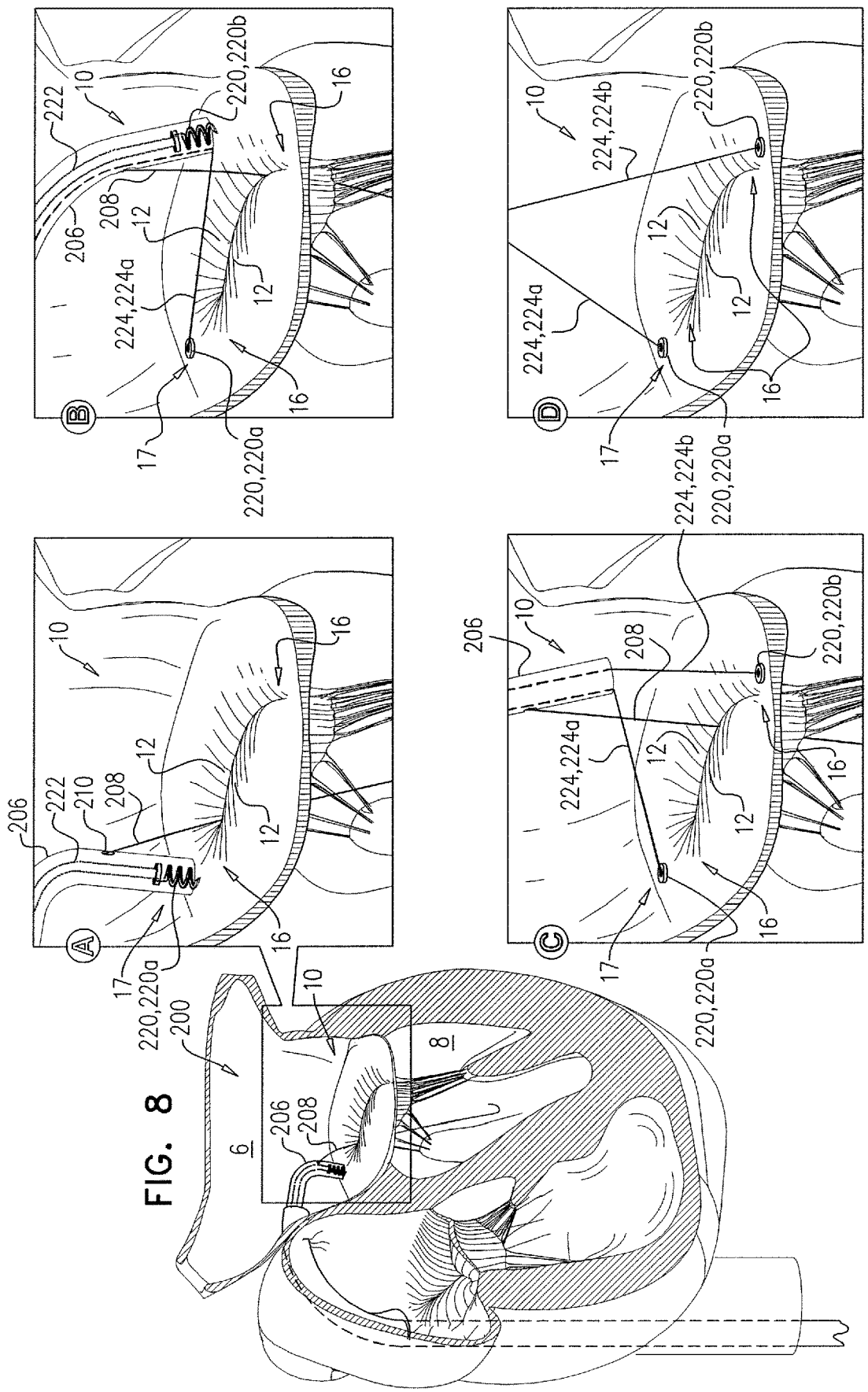

FIG. 11B
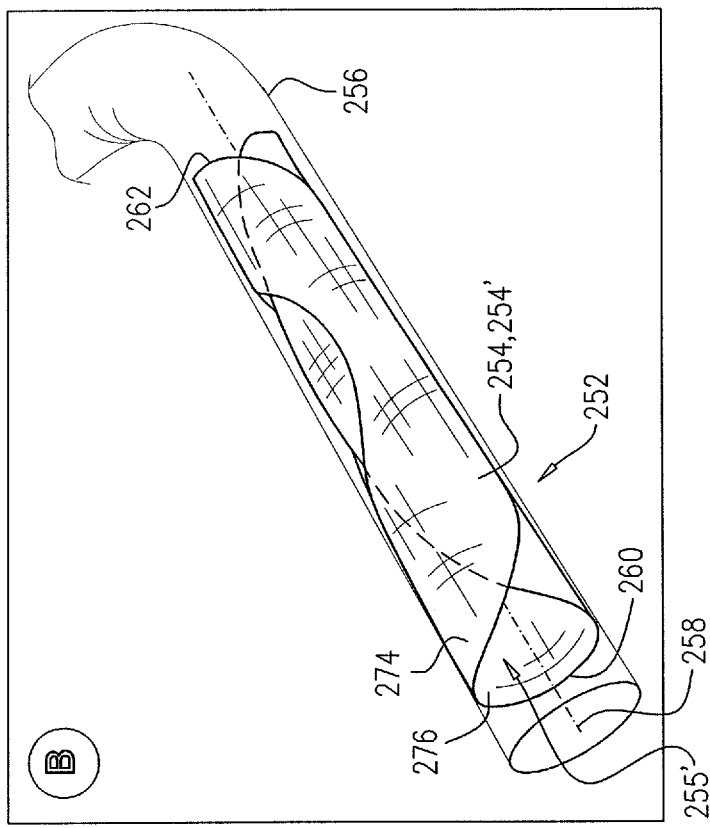
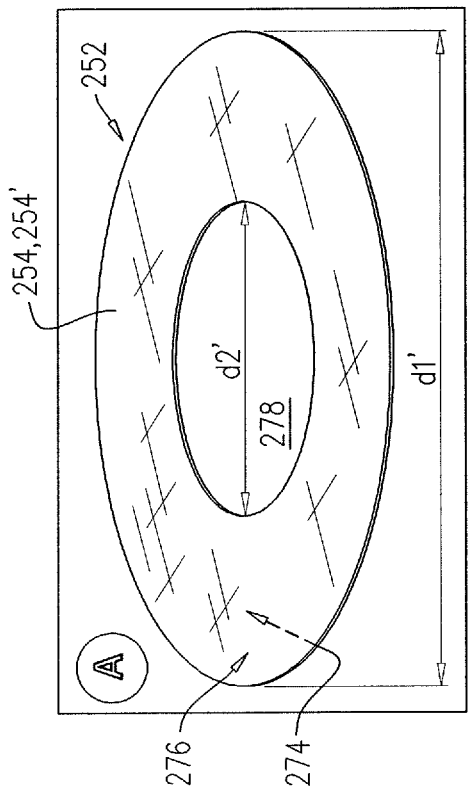
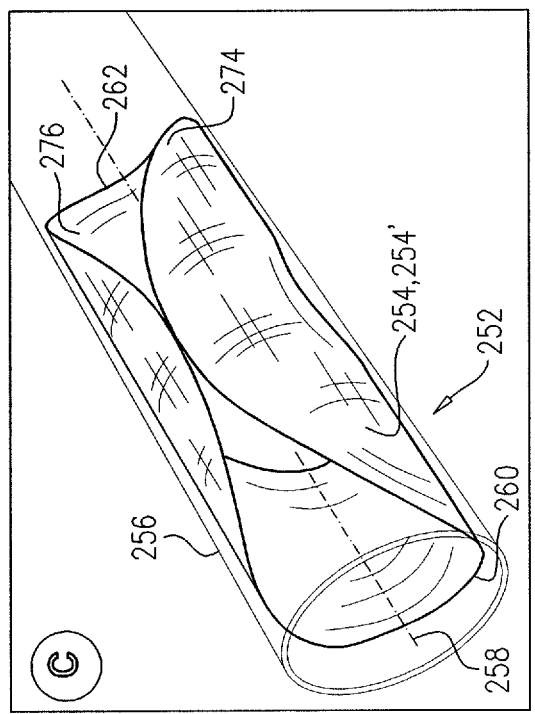

FIG. 11C
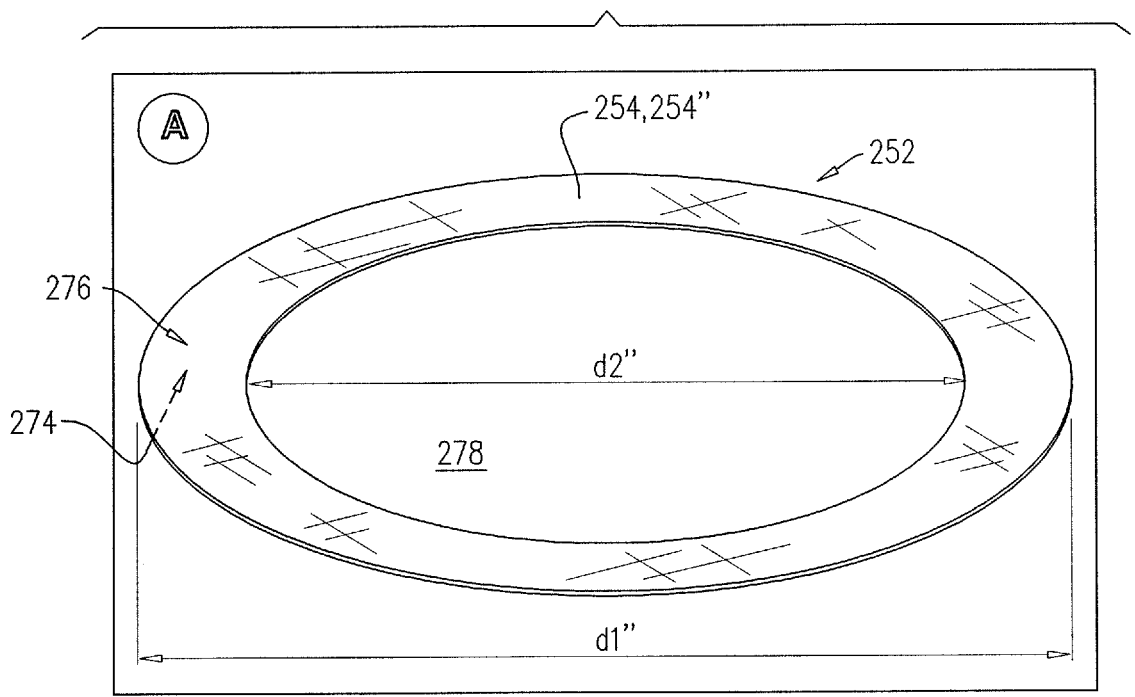
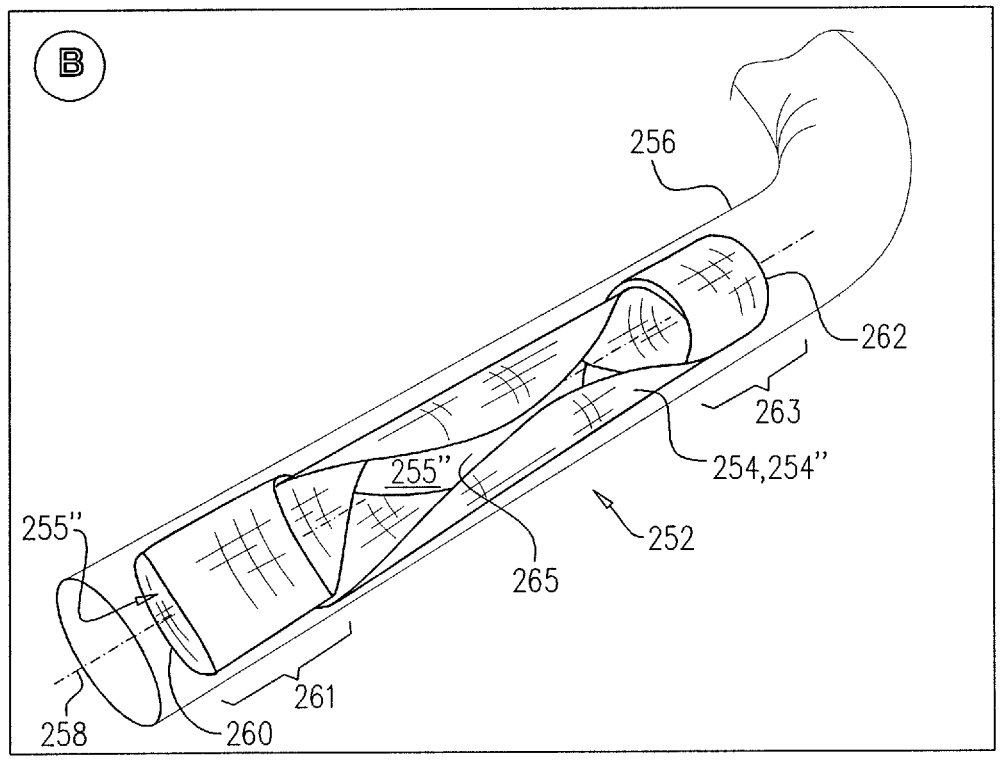

US 10,835,377 B2

ROLLED PROSTHETIC VALVE SUPPORT

CROSS-REFERENCES TO RELATED APPLICATIONS

The present application is a Continuation of U.S. patent application Ser. No. 14/161,921 to HaCohen et al., filed Jan. 23, 2014, and entitled "Anchoring of prosthetic valve supports," which published as U.S. 2014/0207231, and which:
(1) claims priority from U.S. provisional Patent Application 61/756,034 to Hacohen et al., filed Jan. 24, 2013, and entitled "Tissue-engaging elements"; and U.S. Provisional Patent Application 61/756,049 to Hacohen et al., filed Jan. 24, 2013, and entitled "Ventricularly-anchored prosthetic valve support", and
(2) is related to:
  U.S. patent application publication 201210022639 to Hacohen et al,, filed Jul. 21, 2010 (now U.S. Pat. No. 9,132,009);
  U.S. patent application publication 2012/0022640 to Gross et al., filed Feb. 24, 2011 (now U.S. Pat. No. 8,992,604);
  U.S. patent application Ser. No. 13/811,308 to Gross et al., filed Jan. 21, 2013, which published as U.S. 2013/0172992 (U.S. Pat No. 9,017,399);
  U.S. patent application Ser. No. 13/412,814 to Gross et al., filed Mar. 6, 2012, which published as U.S. 2013/0035759 (now U.S. Pat. No. 8,852,272);
  PCT patent application IL2012/000292 to Gross et al., filed Aug. 5, 2012, which published as WO/2013/021374;
  PCT patent application IL2012/000293 to Gross et al., filed Aug. 5, 2012, which published as WO/2013/021375; and
  a PCT patent application to HaCohen et al., entitled "Ventricularly-anchored prosthetic valves", filed on even date herewith, which was assigned PCT application number IL2014/050087, and which published as WO/2014/115149.
all of which are incorporated herein by reference.

FIELD OF THE INVENTION

Some applications of the present invention relate in general to valve replacement. More specifically, some applications of the present invention relate to prosthetic cardiac valves and techniques for implantation thereof.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications of the invention, a prosthetic valve support is provided for facilitating minimally invasive (e.g., transcatheter and/or transluminal) implantation of a prosthetic valve at a native valve of a subject. The native valve typically has native check valve functionality, i.e., it functions as a check valve. The prosthetic valve support is typically couplable to the native valve (e.g., to leaflets thereof) of the subject without eliminating the check valve functionality of the native valve. The prosthetic valve is subsequently implanted at the native valve by coupling the prosthetic valve to the prosthetic valve support, typically by expanding the prosthetic valve within an opening defined by the prosthetic valve support. The implantation of the prosthetic valve at the native valve replaces, at least in part, the check valve functionality of the native valve with substitute check valve functionality of the prosthetic valve. The prosthetic valve support comprises an upstream support portion, configured to be placed against an upstream surface of the native valve, and shaped to define an opening.

For some applications, the upstream support portion is delivered to the native valve in a delivery configuration (e.g., rolled within a delivery tube), and the tissue-engaging elements comprise tissue anchors that are driven through the upstream support portion and into the annulus of the native valve while at least part of the upstream support portion is still within the delivery tube (e.g., is still in the delivery configuration).

For some applications, the prosthetic valve support comprises tissue-engaging elements, such as clips. For some such applications, the clips comprise two arms, and a fabric which covers the arms, and typically has a greater surface area than the clip arms. The fabric is configured to cushion (e.g., soften and/or disperse) forces applied by the clips on the tissue to which the clip is coupled. The clips of the prosthetic valve support are typically coupled to leaflets of the native valve and are further typically configured to move with the native beating of the leaflets so as not to eliminate the check valve functionality of the native valve.

For some applications, tissue-engaging elements are coupled to the native valve (e.g., to the leaflets thereof) and the upstream support portion is subsequently coupled to the tissue-engaging elements. For such applications, each tissue-engaging element is typically coupled to a longitudinal guide member along (e.g., over) which the upstream support portion is slidable. For some such applications, the tissue-engaging elements comprise clips, configured to be coupled to the leaflets of the native valve. For some such applications, the tissue-engaging elements comprise tissue anchors that are coupled to the annulus.

For some applications in which the tissue-engaging elements comprise tissue anchors, more than one tissue anchor is delivered through one delivery tube. For example, the anchors may each fit snugly through the delivery tube, and be delivered sequentially.

As described hereinabove, a prosthetic valve is typically coupled to the prosthetic valve support after the prosthetic valve support has been coupled to the native valve. For some applications, the prosthetic valve comprises a valve body, and a downstream portion that is configured to inhibit contact between chordae tendineae of the heart and the valve body, such as to prevent damage to the chordae tendineae. Typically, an outer surface of the downstream portion is covered with a fabric. For some applications, the prosthetic valve comprises a valve body that comprises an upstream portion, a downstream portion, and an elastic portion between the upstream portion and the downstream portion. For some such applications, the prosthetic valve is configured to facilitate coupling of a pre-determined portion of the prosthetic valve to the prosthetic valve support (e.g., to the upstream support portion thereof).

There is therefore provided, in accordance with an application of the present invention, apparatus for use with a prosthetic valve at a native valve of a heart of a subject, the apparatus including:

a delivery tube, transluminally advanceable to the heart of the subject;

a prosthetic valve support, configured to support the prosthetic valve at the native valve, and including an upstream support portion, the upstream support portion:

having a working configuration in which the upstream support portion is generally annular and has (1) a tissue-contacting side configured to be placed against an atrial surface of the native valve, and (2) an opposing side, and defines an opening therebetween, and having a delivery configuration in which the upstream support portion defines a channel having a central longitudinal axis, and is configured to be disposed within the delivery tube;

a tissue anchor, configured to be disposed within the channel, and slidable through at least part of the channel; and an anchor driver, slidable within the delivery tube and the channel, and configured to anchor the upstream support portion to tissue of the heart by driving the tissue anchor from the opposing side through the upstream support portion and into the tissue, while at least part of the upstream support portion is disposed within the delivery tube.

In an application, the tissue anchor includes a helical tissue anchor, and is configured to be driven into the tissue by being rotated.

In an application, the upstream support portion is configured to be transitioned from the delivery configuration to the working configuration by being unrolled.

In an application:

in the delivery configuration, the upstream support portion has a distal portion and a proximal portion, and the channel is defined between the distal portion and the proximal portion, the anchor includes a first anchor, and the anchor driver is configured to anchor the distal portion of the upstream support portion to the tissue by driving the first anchor through the distal portion of the upstream support portion, and the apparatus is configured such that:

the proximal portion of the upstream support portion is configured to be at least partly exposed from the delivery tube subsequently to the anchoring of the distal portion, and the apparatus further includes a second anchor, configured to be driven through the proximal portion of the upstream support portion and into the tissue subsequently to the exposing.

In an application, in the delivery configuration, the upstream support portion has a distal portion and a proximal portion, and shapes the channel to be an uninterrupted lumen between the distal portion and the proximal portion.

In an application, the anchor driver is configured to slide the tissue anchor through at least most of the channel before driving the anchor through the upstream support portion.

In an application, the delivery tube is configured to be transluminally advanced while the upstream support portion is disposed within a distal portion of the delivery tube, and while the tissue anchor and a distal portion of the anchor driver are disposed within the channel.

In an application, the delivery tube is configured to retain the upstream support portion in the delivery configuration, and the upstream support portion is configured to automatically transition toward the working configuration upon becoming exposed from the delivery tube.

In an application, in the delivery configuration, at any given part of the upstream support portion, the opposing side of the upstream support portion is disposed closer to the central longitudinal axis than is the tissue-contacting side.

In an application, while the upstream support portion is in the delivery configuration and disposed within the delivery tube, the channel shares a common central longitudinal axis with the delivery tube, and the anchor driver is configured to drive the tissue anchor through the upstream support portion by moving the tissue anchor along the common central longitudinal axis.

In an application, the delivery tube is configured to facilitate the driving of the tissue anchor through the upstream support portion by deflecting a portion of the prosthetic valve support to intersect with the common central longitudinal axis by pressing the portion of the prosthetic valve support against the tissue.

There is further provided, in accordance with an application of the present invention, a method for anchoring a prosthetic valve support to a native valve of a heart of a subject, the native valve having an annulus and a plurality of leaflets, the prosthetic valve support including an upstream support portion that is configured to be placed against an atrial surface of the annulus, the method including:

transluminally advancing, to the heart of the subject, the upstream support portion, while the upstream support portion (1) is in a delivery configuration thereof in which the upstream support portion has a distal portion and a proximal portion, and defines a channel therebetween, and (2) is disposed within a delivery tube;

advancing, out of a distal end of the delivery tube, the distal portion of the upstream support portion;

using an anchor driver at least a distal end of which is disposed within the channel, anchoring the distal portion of the upstream support portion to a site of the annulus by driving an anchor through the distal portion of the upstream support portion and into the site; and subsequently, facilitating transition of the upstream support portion into a working configuration in which the upstream support portion is generally annular, and is disposed against the annulus.

In an application, transluminally advancing the upstream support portion includes transluminally advancing the delivery tube while the upstream support portion is disposed within a distal portion of the delivery tube, and while the tissue anchor and a distal portion of the anchor driver are disposed within the channel.

In an application, facilitating transition of the upstream support portion into the working configuration includes facilitating unrolling of the upstream support portion into the working configuration.

In an application, facilitating transition of the upstream support portion into the working configuration includes exposing the upstream support portion from the delivery tube such that the upstream support portion transitions automatically into the working configuration.

In an application, the method further includes advancing the tissue anchor through at least most of the channel prior to anchoring the distal portion.

In an application:

the anchor includes a first anchor, and the site includes a first site, and the method further includes, subsequently to anchoring the distal portion, sliding the anchor driver proximally within the channel and subsequently anchoring, using a second anchor, a proximal portion of the upstream support portion to a second site of the annulus.

In an application, the method further includes pressing the distal portion against the site such that a plane of the distal portion is disposed at greater than 45 degrees with respect to a longitudinal axis of the delivery tube.

In an application:

while the upstream support portion is in the delivery configuration and disposed within the delivery tube, the channel shares a common central longitudinal axis with the delivery tube, and driving the anchor through the distal portion includes driving the anchor through the distal wall by moving the tissue anchor along the common central longitudinal axis.

In an application:

the method further includes pressing the distal portion against the site such that the distal portion deflects with respect to a central longitudinal axis of the channel, and driving the tissue anchor through the distal portion includes moving the anchor driver distally within the channel while the distal portion is pressed against the site.

There is further provided, in accordance with an application of the present invention, a method for anchoring a prosthetic valve support to a native valve of a heart of a subject, the native valve having an annulus and a plurality of leaflets, the prosthetic valve support including an upstream support portion that is configured to be placed against an atrial surface of the annulus, the method including:

transluminally advancing, to the heart of the subject, the upstream support portion, while the upstream support portion (1) is in a delivery configuration thereof in which the upstream support portion generally defines a tube that defines a channel, and (2) is disposed within a delivery tube;

advancing, out of a distal end of the delivery tube, a distal portion of the upstream support portion in the delivery configuration thereof;

anchoring the distal portion to a first site of the annulus using an anchor that is reversibly coupled to an anchor driver, by moving the anchor driver distally within the channel of the tube defined by the upstream support portion; and facilitating unrolling of the upstream support portion into a deployed configuration in which the upstream support portion is generally annular, and is disposed against the annulus.

In an application, the anchor includes a first anchor, and the method further includes anchoring, using a second anchor, a proximal portion of the upstream support portion to a second site of the annulus.

In an application, anchoring the distal portion of the upstream support portion to the first site includes bending the distal portion by pressing the distal portion against the first site, such that moving the anchor driver distally within the channel of the tube defined by the upstream support portion moves the anchor through the distal portion.

In an application, the method further includes pressing the distal portion against the first site such that a plane of the distal portion is disposed at greater than 45 degrees with respect to a longitudinal axis of the delivery tube.

There is further provided, in accordance with an application of the present invention, apparatus for facilitating implantation of an implant at a native valve of a heart of a subject, the apparatus including a tissue-engaging element, the tissue-engaging element including:

a first portion of the apparatus, including:
at least one arm, having:
a first end, a second end, and a longitudinal axis therebetween, and
a face that has a length along the longitudinal axis of the arm, and a width that is orthogonal to the length, the length and the width defining an area of the face, and
a fabric, coupled to the arm so as to have a length and a width that define an area of the fabric, the area of the fabric being greater than the area of the face; and
a second portion of the apparatus,
the first end of the arm of the first portion being articulatably coupled to the second portion at a hinge region, and the tissue-engaging element being configured to sandwich tissue in a vicinity of the native valve between the fabric and the second portion of the apparatus.

In an application, the tissue-engaging element is configured to sandwich tissue of the native valve between the fabric and the second portion of the apparatus.

In an application, the area of the fabric is more than twice as great as the area of the face.

In an application, the fabric entirely covers the face.

In an application, the apparatus further includes the implant, and the second portion of the apparatus includes a portion of the implant.

In an application, the fabric is generally shaped to define a saddle shape having a saddle point, the saddle point being disposed in a vicinity of the hinge region.

In an application:

the arm of the first portion includes a first arm, and the face of the first arm includes a first face, the second portion of the apparatus includes a second arm, having:
a first end, a second end, and a longitudinal axis therebetween, and
a second face that has a length along the longitudinal axis of the second arm, and a width that is orthogonal to the length of the face of the second arm, the length and the width of second face defining an area of the second face,
the first end of the second arm is articulatably coupled to the first end of the first arm at the hinge region,
the fabric is coupled to the first arm and to the second arm, and is disposed over the first face and the second face, and
the area of the fabric is greater than the sum of the area of the first face and the area of the second face.

In an application, the first face extends laterally from the longitudinal axis of the first arm, the second face extends laterally from the longitudinal axis of the second arm, and the fabric extends further from the longitudinal axis of each of the first and second arms than does the width of the first and second faces, respectively.

In an application, the fabric extends, from the hinge region, further along the longitudinal axis of the first arm than does the first face.

In an application, a portion of the fabric is disposed over a second end of the first arm.

In an application, the portion of the fabric that is disposed over the second end of the first arm defines at least part of a cushion.

In an application, the cushion extends, from the second end of the first arm, away from the second arm.

There is further provided, in accordance with an application of the present invention, apparatus, for implantation at a native valve of a heart of a subject, the native valve including at least a first valve leaflet and a second valve leaflet, each leaflet being coupled to a respective plurality of chordae tendineae, the apparatus including:

a prosthetic valve, including:
  a tubular valve body, having an upstream end and a downstream end, and configured to be placed between the leaflets of the native valve;
  at least one valve member, configured to facilitate flow of blood of the subject from the upstream end of the valve body to the downstream end of the valve body, and to inhibit flow of the blood from the downstream end of the valve body to the upstream end of the valve body; and a downstream portion:
  coupled to the downstream end of the valve body,
  extending away from the downstream end of the valve body,
  configured to be placed between the plurality of chordae tendineae coupled to the first valve leaflet, and the plurality of chordae tendineae coupled to the second valve leaflet, and
  configured to inhibit contact between the chordae tendineae and the valve body.

In an application, the downstream portion includes a frame, and at least an outer surface of the frame is covered with a covering.

In an application, the downstream portion is tubular, and the downstream portion and the valve body define a continuous lumen therethrough.

In an application, the heart of the subject includes a plurality of papillary muscles, and at least part of the downstream portion is configured to be placed in contact with at least one of the papillary muscles.

In an application, the downstream portion includes one or more protrusions, each protrusion extending away from the downstream end of the valve body.

In an application, the valve body has a longitudinal axis therethrough, and includes a circumferential lateral wall that defines a curved plane that circumscribes the longitudinal axis, and the protrusions lie on the plane.

In an application, each protrusion has a transverse cross-sectional shape of an arc, and the arc of each protrusion lies on the curved plane defined by the valve body.

There is further provided, in accordance with an application of the present invention, apparatus, for implantation at a native valve of a heart of a subject, the native valve being disposed between an atrium and a ventricle of the heart, the apparatus including:
  a tubular valve body:
    having an upstream portion, configured to be disposed in the atrium of the heart of the subject,
    having a downstream portion, configured to be disposed in the ventricle of the subject,
    having an elastic portion, disposed between the upstream portion and the downstream portion, and elastically coupling the upstream portion to the downstream portion, and
    shaped to define a continuous lumen through the upstream portion, the elastic portion, and the downstream portion; and
  at least one valve member, disposed in the lumen of the valve body, and configured to facilitate flow of blood of the subject from the upstream portion of the valve body to the downstream portion of the valve body, and to inhibit flow of the blood from the downstream portion of the valve body to the upstream portion of the valve body.

In an application, the at least one valve member is coupled to the downstream portion of the valve body.

In an application, the native valve includes a plurality of native leaflets, and the downstream portion of the valve body is configured to be coupled to the native leaflets.

In an application, the apparatus further includes a plurality of clips, configured to facilitate the coupling of the downstream portion of the valve body to the native leaflets.

In an application, each clip:
  includes at least two clip arms, articulatably coupled to each other, and
  is reversibly closeable.

In an application, the clips are coupled to the downstream portion of the valve body, and the downstream portion of the valve body is configured to be coupled to the native leaflets by the clips being coupled to the native leaflets.

In an application, each clip of the plurality of clips is articulatably coupled to the downstream portion of the valve body.

In an application, the native valve includes an annulus having an upstream surface, and the apparatus further includes a prosthetic valve support:
  including (1) an upstream support portion, configured to be placed against the upstream surface of the annulus of the native valve, and (2) the plurality of clips, coupled to the upstream support portion, and
  shaped to define an opening therethrough that is configured to receive the prosthetic valve,
  and the clips are configured to facilitate the coupling of the downstream portion of the valve body to the native leaflets by coupling the prosthetic valve support to the native leaflets.

There is further provided, in accordance with an application of the present invention, apparatus for facilitating implantation of a prosthetic valve at a native valve of a heart of a subject, the native valve having a plurality of native leaflets, the apparatus including:
  at least one tissue-engaging element, configured to be transluminally delivered to the native valve, and to be coupled to a native leaflet of the subject;
  an upstream support portion, configured to be transluminally delivered to the native valve, and to be intracorporeally coupled to the tissue-engaging element;
  at least one locking element, configured to intracorporeally couple the tissue-engaging element to the upstream support portion such that the tissue-engaging element is movable with respect to the upstream support portion.

In an application, the tissue-engaging element includes a clip, having at least a first arm and a second arm, the first and second arms being articulatably coupled to each other, and the clip is reversibly openable and closeable.

In an application:
  the first arm has a first face and the second arm has a second face,
  the tissue-engaging element includes a fabric that is coupled to the first arm and to the second arm, and is disposed over the first face and the second face, and
  the fabric defines an area that is greater than the sum of the area of the first face and the area of the second face.

In an application, the apparatus further includes a clip controller, configured to interface with the clip, and to facilitate the reversible opening and closing of the clip.

In an application, the apparatus further includes at least one flexible longitudinal guide member, and the apparatus is configured such that, when the locking element couples the tissue-engaging element to the upstream support portion, at least a portion of the flexible longitudinal guide member is disposed between the tissue-engaging element and the upstream support portion.

In an application:
  the flexible longitudinal guide member is coupled to the locking element and to the tissue-engaging element, the locking element is configured to couple the tissue-engaging element to the upstream support portion by the locking element being coupled to the upstream support portion, and flexibility of the at least the portion of the flexible longitudinal guide member facilitates the coupling of the tissue-engaging element to the upstream support portion such that the tissue-engaging element is movable with respect to the upstream support portion.

There is further provided, in accordance with an application of the present invention, a method for anchoring a prosthetic valve support to a native valve of a subject, the native valve having an annulus and a plurality of leaflets, the method including:

transluminally advancing a delivery tube such that a distal end of the delivery tube is disposed in a vicinity of a first site of the annulus;

advancing a first anchor distally through the delivery tube by advancing an anchor driver through the delivery tube, the anchor driver having a distal end to which the first anchor is reversibly coupled, and the first anchor being coupled to a distal end of a first guide member;

anchoring the first anchor to tissue of the first site of the annulus using the anchor driver;

subsequently, decoupling the anchor driver from the first anchor, and proximally withdrawing the anchor driver such that at least a portion of the first guide member remains disposed within the delivery tube, and such that the distal end of the first guide member remains coupled to the first anchor;

subsequently, advancing a second anchor through the delivery tube such that the second anchor passes at least the portion of the first guide member, the second anchor being coupled to a distal end of a second guide member;

positioning the distal end of the delivery tube in a vicinity of a second site of the annulus; and anchoring the second anchor to tissue of the second site of the annulus;

sliding the prosthetic valve support distally over the first guide member and the second guide member; and anchoring the prosthetic valve support to the native valve by inhibiting further sliding of the prosthetic valve support with respect to the first guide member and the second guide member.

In an application:

transluminally advancing the delivery tube includes transluminally advancing a delivery tube through which the first anchor fits snugly and through which the second anchor fits snugly, advancing the first anchor distally through the delivery tube includes advancing the first anchor distally through the delivery tube in which the first anchor fits snugly, and advancing the second anchor distally through the delivery tube includes advancing the second anchor distally through the delivery tube in which the second anchor fits snugly.

In an application, advancing the anchor driver through the delivery tube includes advancing the anchor driver through a delivery tube through which the anchor driver fits snugly.

In an application, advancing anchor driver includes advancing an anchor driver that has a transverse cross-sectional area that is more than twice as great as a transverse cross-sectional area of the first guide member.

In an application, anchoring the first anchor, anchoring the second anchor, and anchoring the prosthetic valve support include anchoring the first anchor, anchoring the second anchor, and anchoring the prosthetic valve support without eliminating movement of the leaflets of the native valve.

In an application, anchoring the first anchor, anchoring the second anchor, and anchoring the prosthetic valve support include anchoring the first anchor, anchoring the second anchor, and anchoring the prosthetic valve support without engaging the leaflets of the native valve.

In an application, anchoring the first anchor at the first site of the annulus includes anchoring the first anchor at a first site of the annulus that is in the vicinity of a first commissure of the native valve, and anchoring the second anchor at the second site of the annulus includes anchoring the second anchor at a second site of the annulus that is in the vicinity of a second commissure of the native valve.

In an application, the method further includes advancing a guidewire to the first commissure of the native valve, the delivery tube being shaped to define a lateral opening through which the guidewire is slidable, and transluminally advancing the delivery tube to the first site of the annulus includes sliding the delivery tube over the guidewire.

In an application, transluminally advancing the delivery tube to the first site that is in the vicinity of the first commissure includes transluminally advancing the delivery tube to a first site that is a distance from the first commissure, the distance of the first site from the first commissure being at least in part dependent on a distance between the distal end of the delivery tube and the lateral opening of the delivery tube.

The present invention will be more fully understood from the following detailed description of applications thereof, taken together with the drawings, in which:

BRIEF DESCRIPTION OF THE DRAWINGS

FIGS. 1A-C and 2 are schematic illustrations of a system comprising an implant comprising one or more tissue-engaging elements, in accordance with some applications of the invention;

FIGS. 5A-D are schematic illustrations of a system comprising an upstream support portion, a plurality of tissue-engaging elements, a locking element, and a prosthetic valve, in accordance with some applications of the invention;

FIGS. 6 and 7A-B are schematic illustrations of a prosthetic valve having a tubular valve body that comprises an upstream portion, a downstream portion, and an elastic portion disposed between the upstream portion and the downstream portion, in accordance with some applications of the invention;

FIGS. 8-10 are schematic illustrations of a system for delivering and anchoring to a native valve, a prosthetic valve support comprising an upstream support portion, in accordance with some applications of the invention; and FIGS. 11A-C are schematic illustrations of a system for delivering and anchoring to a native valve, a prosthetic valve support comprising an upstream support portion, in accordance with some applications of the invention.

DETAILED DESCRIPTION OF EMBODIMENTS

Figure 1A:
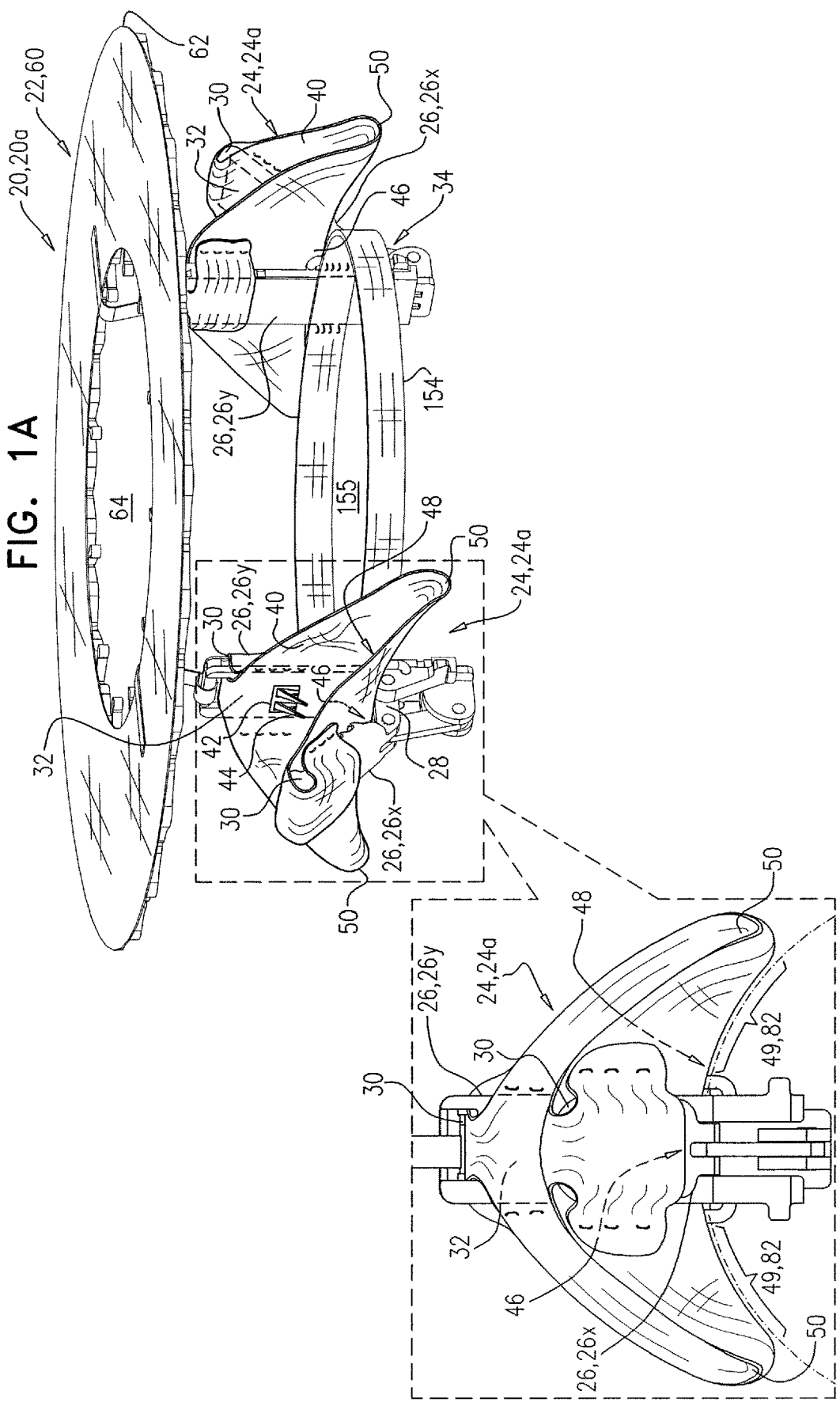
Figure 2:
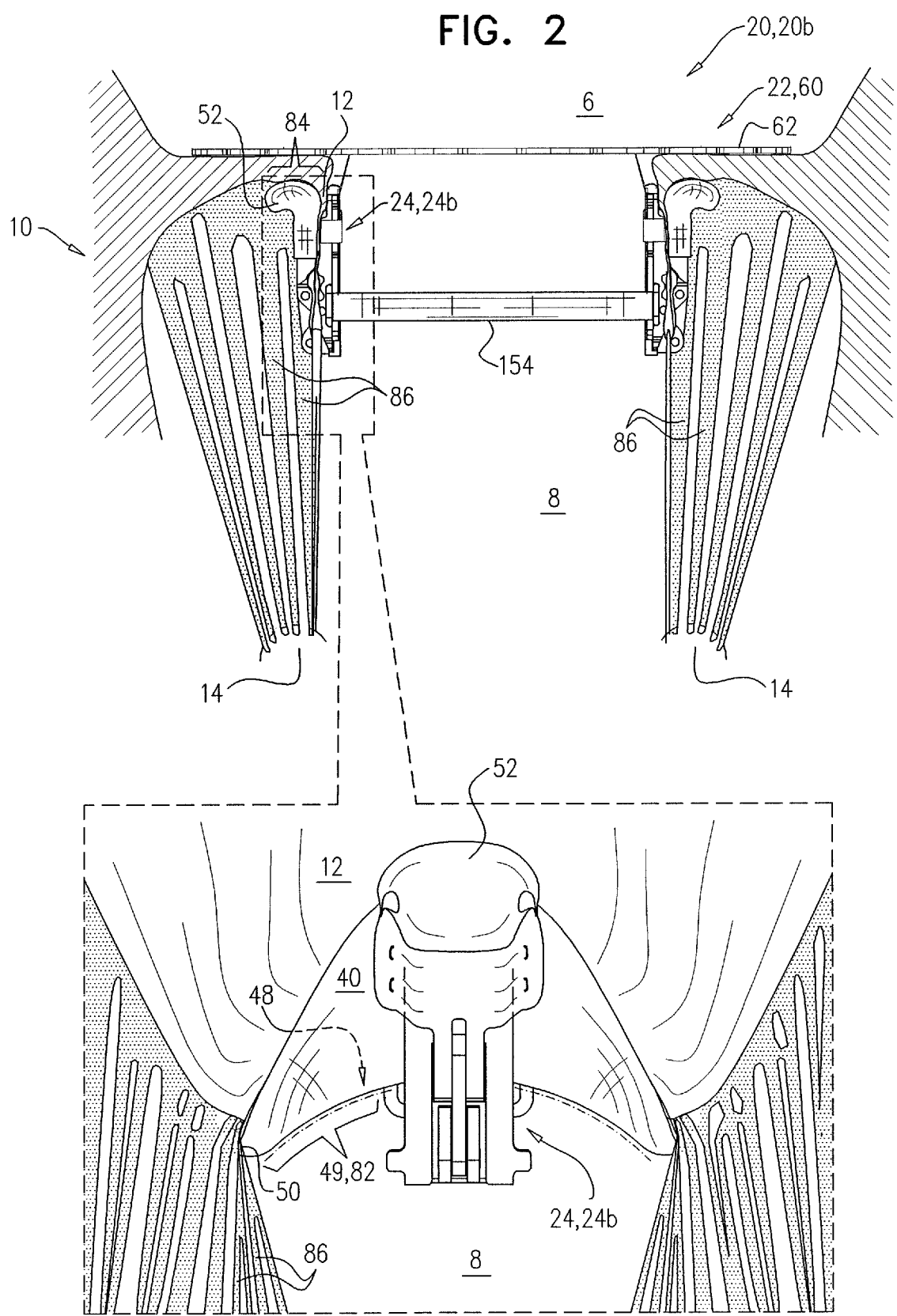

Reference is made to FIGS. 1A-C and 2, which are schematic illustrations of a system 20 comprising an implant 22, and apparatus for facilitating implantation of the implant at a native heart valve 10 of a subject, the apparatus comprising a tissue-engaging element 24, in accordance with some applications of the invention. FIG. 1A shows system 20 comprising a system 20a, and tissue-engaging element 24 comprising a tissue-engaging element 24a, in accordance with some applications of the invention. FIG. 1B shows system 20 comprising a system 20b, and tissue-engaging element 24 comprising a tissue-engaging element 24b, in accordance with some applications of the invention. FIG. 1C shows system 20 comprising a system 20c, and tissue-engaging element 24 comprising a tissue-engaging element 24c, in accordance with some applications of the invention. FIG. 2 shows system 20b having been implanted at native valve 10, in accordance with some applications of the invention.

Tissue-engaging element 24 (e.g., tissue-engaging elements 24a, 24b, and 24c) comprises at least one arm 26. Typically, element 24 comprises two arms 26 (e.g., a first arm 26x and a second arm 26y), which are articulatably coupled to each other at a hinge region 34. Each arm 26 has a length from a first end 28 thereof at hinge region 34, to a second end 30 thereof, and a longitudinal axis therebetween. Each arm 26 also has a face 32, which has a length along the longitudinal axis of the arm, a width that is orthogonal to the length, and an area defined by the width and the length.

Tissue-engaging element 24 is configured to sandwich tissue in the vicinity of the native heart valve using the at least one arm 26. Typically, element 24 is configured to sandwich the tissue between first arm 26x and second arm 26y. Alternatively, element 24 may comprise only one arm (e.g., arm 26x), coupled to another portion of the apparatus (e.g., a portion of implant 22), and may be configured to sandwich the tissue between arm 26x and the other portion of the apparatus. Typically, and as shown in FIG. 2, element 24 is configured to sandwich, between arms 26, tissue of the native heart valve, such as tissue of a native leaflet 12 of the native heart valve.

Tissue-engaging element 24 further comprises a fabric 40, coupled to arm 26 so as to have a length and a width that define an area of the fabric (e.g., an area of the fabric that is disposed over face 32). Typically, the area of fabric 40 is greater than the area of face 32, such that part of the fabric is disposed over face 32, and part of the fabric extends past the face. For example, FIGS. 1A and 1B show fabric 40 of tissue-engaging elements 24a and 24b, respectively, extending laterally (i.e., width-ways) from face 32 (that is, the width of the fabric is greater than the width of the face, and the fabric extends further from the longitudinal axis of the arm, than does the face). Similarly, FIGS. 1B and 1C show fabric 40 of tissue-engaging elements 24b and 24c, respectively, extending away from second end 30 of arm 26x (that is, the length of fabric 40 is greater than the length of face 32, and the fabric extends further along the longitudinal axis of the arm from the hinge, than does the face). Fabric 40 is configured to cushion (e.g., soften and/or disperse) forces applied by element 24 on the tissue to which element 24 is coupled.

It is to be noted that throughout this patent application, including the specification and the claims, the term "fabric" typically means a woven fabric, but may also include other sheet-like materials, such as sheets of polymer and/or silicone.

For some applications, the area of fabric 40 is more than twice as great as the area of face 32. For some applications, the fabric entirely covers face 32. Alternatively, fabric 40 may be shaped to define a hole 42 through which a portion of arm 26 (e.g., a portion of face 32 thereof) may contact the tissue being sandwiched (e.g., the tissue of the native leaflet). For example, and as shown in FIGS. 1A-C, arm 26y may be shaped to define one or more barbs 44, configured to protrude through hole 42, and pierce the tissue being sandwiched, so as to facilitate gripping of the tissue.

Typically, tissue-engaging elements 24 comprise two arms 26 (e.g., arms 26x and 26y) and two respective faces 32, and fabric 40 spans both faces, and is bent (e.g., folded) to define a trough 48 in the vicinity of hinge region 34, thereby forming a clip with two tissue-engaging surfaces comprising fabric 40, and corners 50 that define respective ends of the trough. Typically, the area of fabric 40 is greater than (e.g., more than twice as great as) the sum of the respective areas of both faces 32, and thereby at least part (e.g., more than half) of fabric 40 is not directly backed by an arm (e.g., a face thereof), thereby providing flexibility to the clip. For some applications, and as shown in FIGS. 1A-B for tissue-engaging elements 24a and 24b, fabric 40 is shaped, and coupled to arms 26, so as to define a saddle shape. A saddle point 46 of the saddle shape is typically disposed in the vicinity of hinge region 34 (e.g., at hinge region 34), such that "wings" 49 of the fabric protrude laterally (i.e., width-ways) from faces 32, and trough 48 curves downward toward corners 50.

As shown in the magnified area of FIG. 2, wings 49 of fabric 40 that protrude laterally from arms 26 engage the tissue being sandwiched (e.g., leaflets 12), and provide lateral flexible coupling regions 82 that cushion (e.g., soften and/or disperse) forces applied by tissue-engaging element 24 on leaflet 12. Typically, and as shown in the magnified area of FIG. 2, element 24 is coupled to leaflet 12 such that, for at least some chordae tendineae 86 that are coupled to the leaflet being sandwiched, the respective points at which the chordae tendineae are coupled to the leaflet are disposed within trough 48 of fabric 40, and the chordae tendineae extend out of corners 50, and toward the papillary muscle 14 to which they are coupled.

Typically, and as shown in FIGS. 1A-C, fabric 40 is disposed over second end 30 of at least arm 26x. For some applications, and as shown in FIGS. 1B-C, fabric 40 is shaped to define a cushion 52 in the vicinity of second end 30 of arm 26x. For some applications, cushion 52 comprises a soft material (e.g., enveloped by fabric 40). For some applications, and as shown in FIGS. 1B-C, cushion 52 extends from second end 30 of arm 26x, away from arm 26y. Cushion 52 is configured to cushion (e.g., soften and/or disperse) forces applied by element 24 on the tissue to which element 24 is coupled. As shown in FIG. 2, cushion 52 provides a cushioning region 84 that cushions (e.g., softens and/or disperses) forces applied by tissue-engaging element 24 on leaflet 12.

For some applications, and as shown in FIGS. 1A-C, implant 22 comprises a prosthetic valve support 60, comprising an upstream support portion 62, configured to be placed against an upstream surface of an annulus of the native valve, e.g., as shown in FIGS. 2A-B, and shaped to define an opening 64 that is configured to receive a prosthetic valve. For some applications, prosthetic valve support 60 comprises a stabilizing member 154, described in more detail hereinbelow with reference to FIGS. 5A-D, typically coupled to elements 24. For some applications, implant 22 comprises a prosthetic valve.

For some applications, tissue-engaging elements 24 are articulatably coupled to upstream support portion 62 such that, when prosthetic valve support 60 is coupled to the native valve, native movement (e.g., beating) of the leaflets of native valve 10 is not eliminated, and thereby check-valve functionality of the native valve is not eliminated. For some such applications, prosthetic valve support is thereby implantable without the use of cardiopulmonary bypass.

Reference is made to FIGS. 3A-B and 4A-B, which are schematic illustrations of apparatus 100 comprising a prosthetic valve 102 that comprises a tubular valve body 104 and a downstream portion 106, in accordance with some applications of the invention. Prosthetic valve 102 comprises at least one valve member, such as a prosthetic leaflet (not shown). Body 104 has an upstream end 108 and a downstream end 110, and downstream portion 106 is coupled to downstream end 110. Downstream portion 106 extends away (i.e., downstream) from downstream end 110, and is configured to inhibit contact between the chordae tendineae and valve body 104.

Figure 3A:
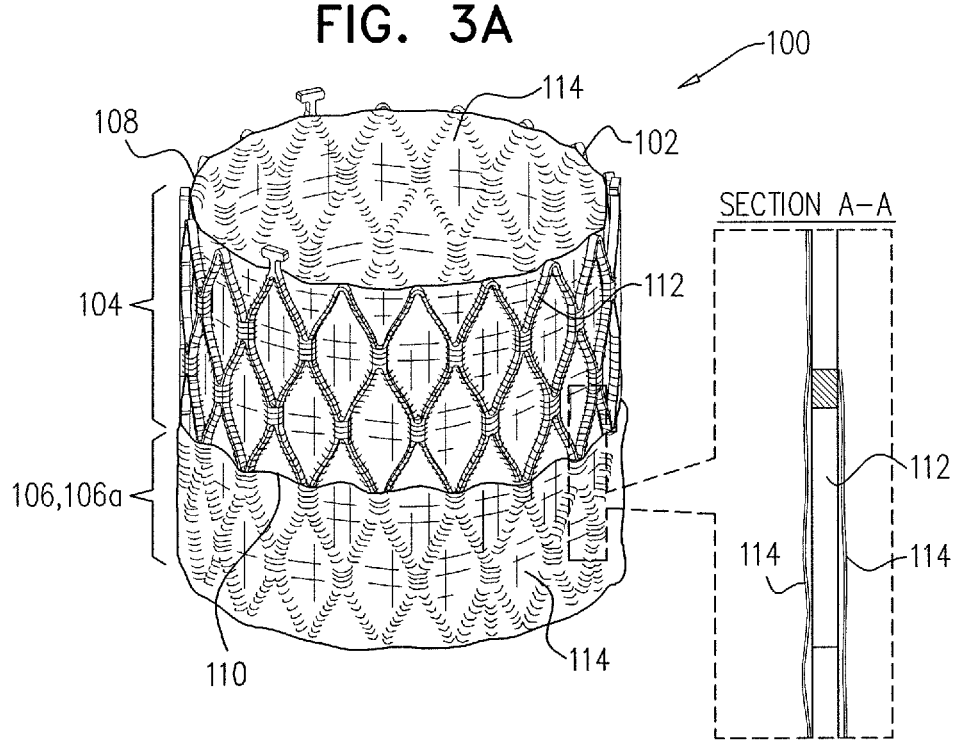
FIGS. 3A-B and 4A-B are schematic illustrations of a prosthetic valve that comprises a tubular valve body and a downstream portion, in accordance with some applications of the invention.
Figure 3B:
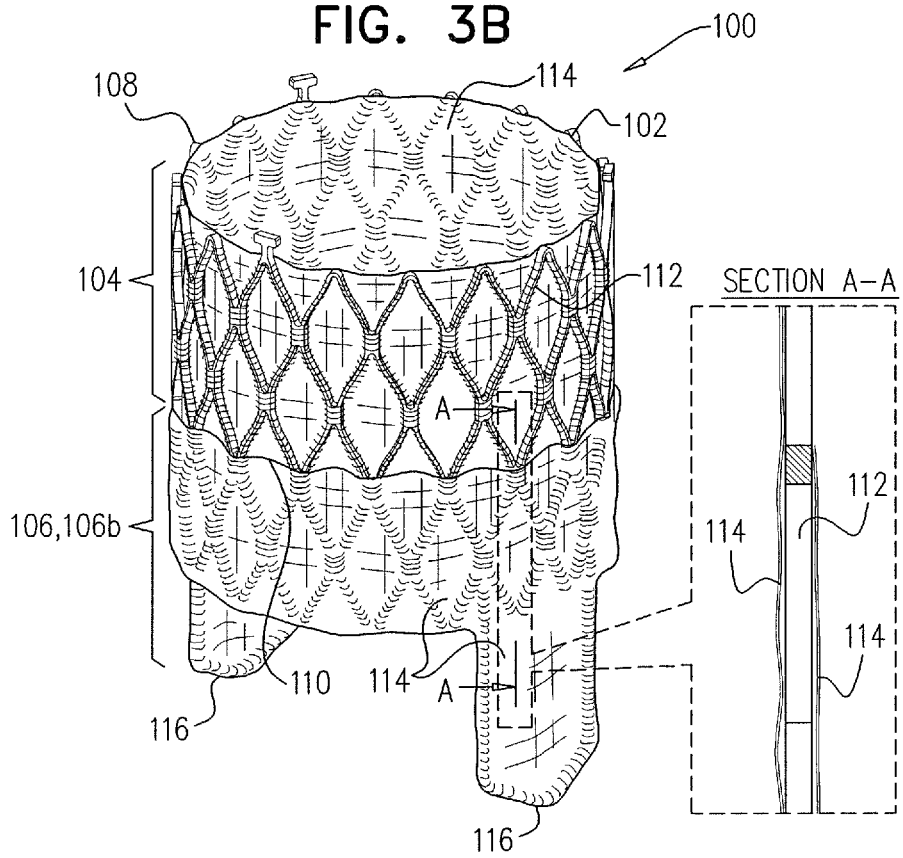

Typically, valve body 104 comprises a frame 112, such as a stent-like wire frame. For some applications, and as shown in FIGS. 3A-B, downstream portion 106 also comprises a frame. For some applications, frame 112 is shaped to define downstream portion 106 (e.g., body 104 and downstream portion 106 comprises respective portions of frame 112).

Typically, apparatus 100 (e.g., prosthetic valve 102 thereof) comprises a covering 114, disposed over (e.g., covering) an inner surface of frame 112. Typically, covering 114 is also disposed over an inner surface of downstream portion 106. Further typically, covering 114 is also disposed over an outer surface of portion 106 (e.g., extends around a distal end of apparatus 100). Sections A-A of FIG. 3A and FIG. 3B show such placements of covering 114.

FIG. 3A shows downstream portion 106 comprising a tubular downstream portion 106a, which is coupled to the downstream end of valve body 104 such that the downstream portion and the valve body define a continuous lumen therethrough. FIG. 3B shows downstream portion 106 a downstream portion 106b that comprises one or more (e.g., two) protrusions 116, each of which protrudes away from the valve body. Typically, protrusions 116 lie on a curved plane defined by valve body 104 (e.g., by a circumferential lateral wall of the valve body, such as that defined by frame 112), e.g., protruding downstream away from the valve body. For some applications, each protrusion 116 has a transverse cross-sectional shape of an arc, and the arc of each protrusion lies on the curved plane defined by valve body 104. For example, downstream portion 106b may resemble tubular downstream portion 106a having had portions thereof cut away.

Figure 4A:
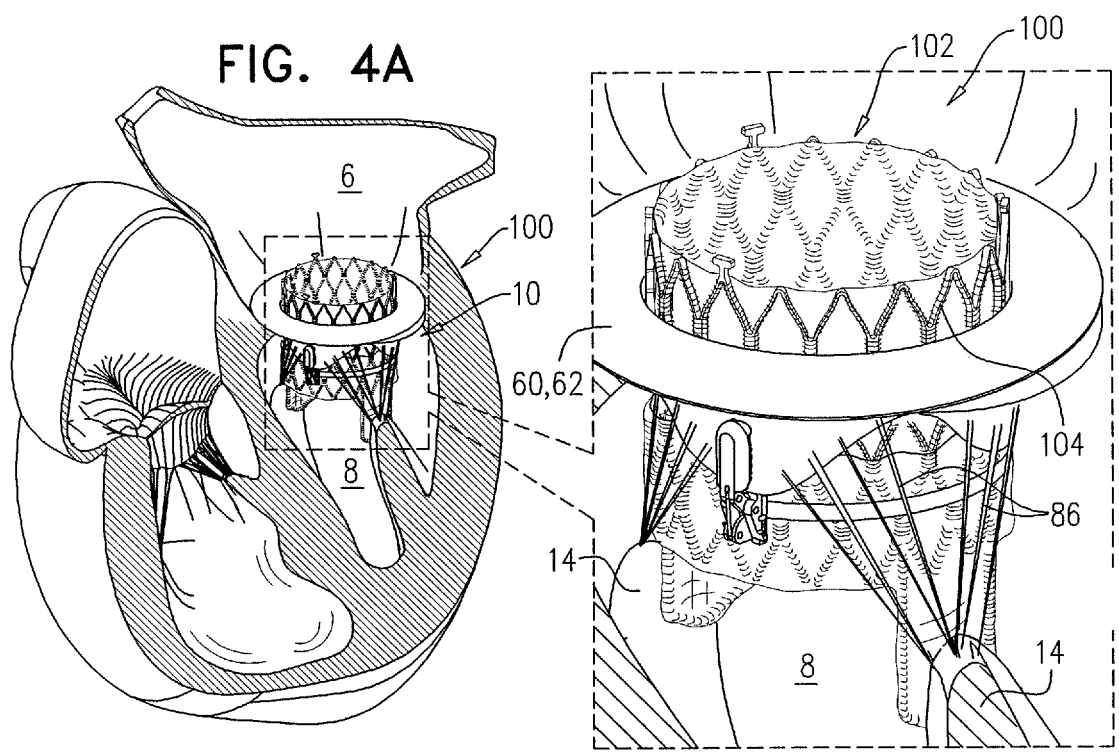
Figure 4B:
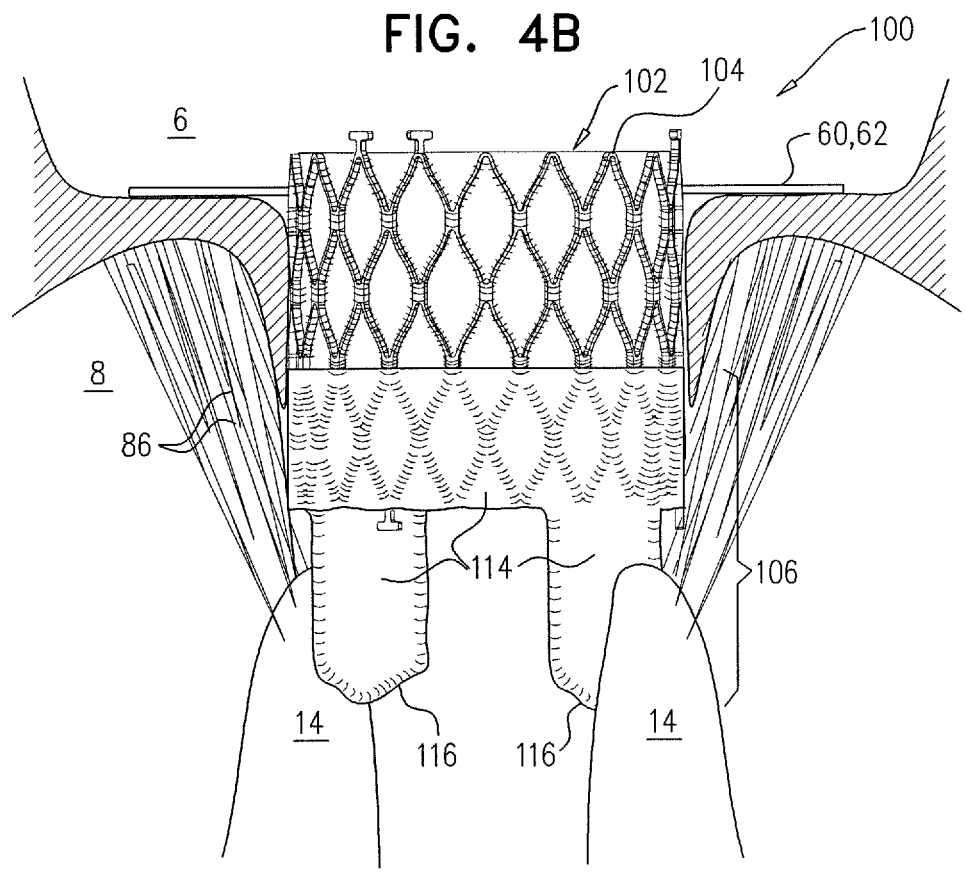

As described hereinabove, downstream portion 106 is configured to inhibit contact between chordae tendineae 86 and valve body 104. As shown in FIG. 4B, for some applications, when apparatus 100 is implanted at the native valve, portion 106 (e.g., protrusions 116 thereof) is in contact with at least one (e.g., two) papillary muscles 14. For some such applications, portion 106 is configured to move the papillary muscles away from each other, and thereby to move at least portions of chordae tendineae 86 away from valve body 104. Covering 114 on the outer surface of portion 106 protects the chordae tendineae and/or papillary muscles from portion 106 (e.g., metallic components of the frame thereof). It is hypothesized that, for some applications, such inhibition of contact between the chordae tendineae and the valve body reduces a likelihood of damage to the chordae tendineae and/or improves blood flow through prosthetic valve 102.

Reference is made to FIGS. 5A-D, which are schematic illustrations of a system 140 comprising an upstream support portion 142, a plurality of tissue-engaging elements 144, a locking element 146, and a prosthetic valve 148, in accordance with some applications of the invention. System 140 is configured such that upstream support portion 142 is couplable to tissue-engaging elements 144 (1) intracorporeally, (2) subsequent to coupling of the tissue-engaging elements to tissue of native valve 10, and (3) prior to coupling of prosthetic valve 148 to the upstream support portion. For some applications of the invention, upstream support portion 142 and tissue-engaging elements 144, when coupled to each other, act as a prosthetic valve support 150.

Figure 5B:
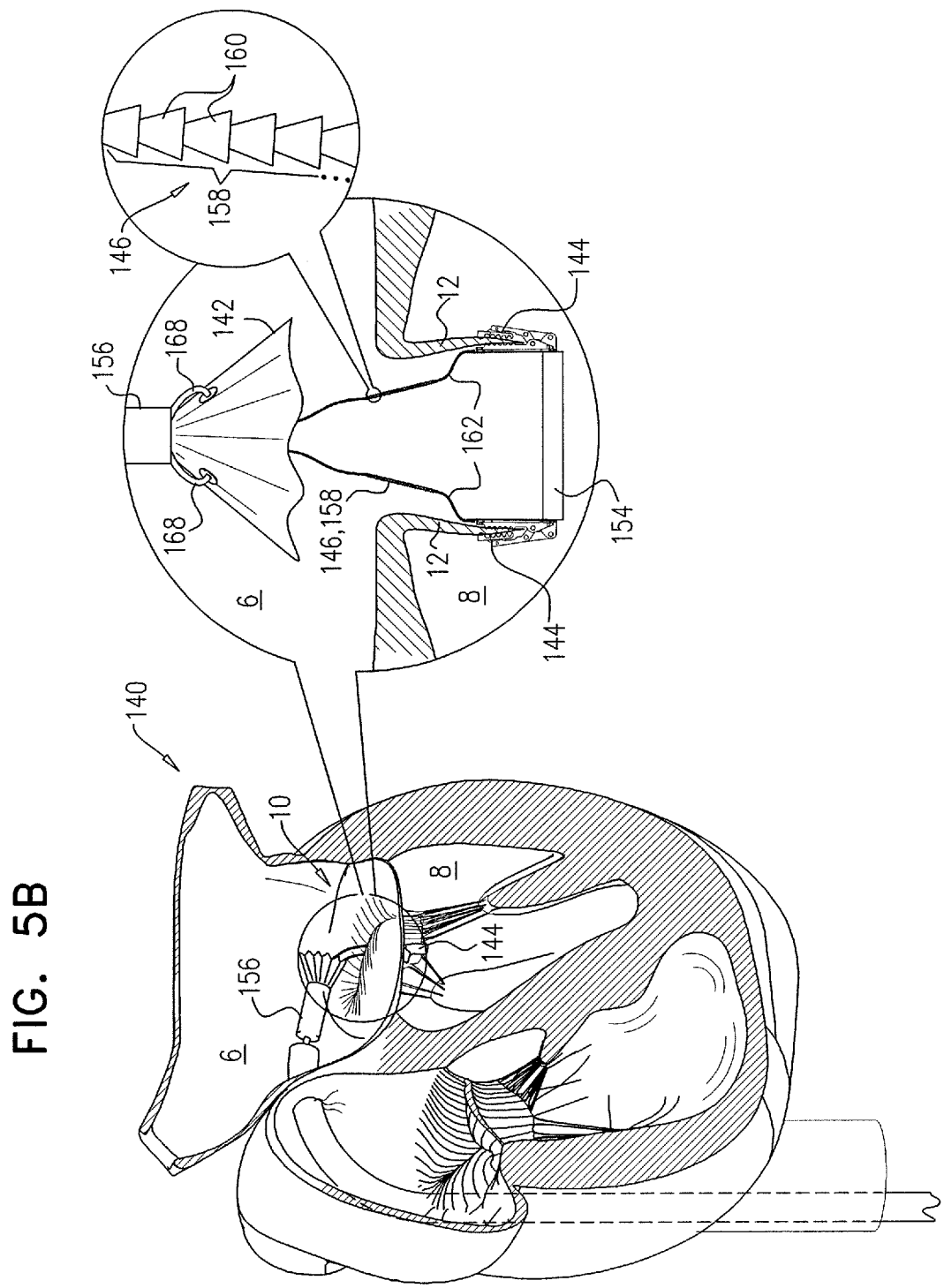

FIG. 5A shows two tissue-engaging elements 144 being coupled to respective leaflets 12 of native valve 10. For some applications, and as shown in FIGS. 5A-D, elements 144 comprise clips that are reversibly openable and closeable, and comprise a clip controller interface that facilitates the reversible opening and closing by interfacing (e.g., reversibly interfacing) with a clip controller 152. For some applications, tissue-engaging elements 144 are delivered within a delivery tube 145. Typically, system 140 (e.g., prosthetic valve support 150 thereof) further comprises a stabilizing member 154, such as a stabilizing band, coupled to tissue-engaging elements 144, and configured to form a ring that is shaped to define an opening 155 therethrough (shown in FIGS. 1A-C for stabilizing member 154 of system 20).

As shown in FIGS. 5A-B, tissue-engaging elements 144 are typically able to move toward and away from each other, following coupling thereof to leaflets 12. It is hypothesized that such movement allows the leaflets of the native valve to continue to move, and therefore facilitates coupling of the tissue-engaging elements to the native valve (e.g., to the leaflets thereof) without eliminating the native valve function. As also shown in FIGS. 5A-B, stabilizing member 154 is typically flexible, so as to facilitate such movement of tissue-engaging elements 144. For example, when the tissue-engaging elements are disposed away from each other (e.g., when leaflets 12 are open; FIG. 5B), member 154 may form the ring that is shaped to define the opening therethrough, and when the tissue-engaging elements are disposed close to each other (e.g., when leaflets 12 are closed; FIG. 5A, mutatis mutandis), member 154 may form a general lemniscate.

FIGS. 5B-C show, subsequent to the coupling of tissue-engaging elements 144 to leaflets 12, upstream support portion 142 being delivered to the upstream (e.g., atrial) surface of the annulus of native valve 10, and coupled to the tissue-engaging elements. Upstream support portion 142 is typically delivered in a compressed (e.g., crimped) configuration within a delivery tube 156. FIG. 5B shows upstream support portion 142 being deployed out of delivery tube 156 and expanding (e.g., automatically expanding) toward an expanded configuration thereof. For some applications, delivery tube 156 comprises delivery tube 155. That is, for some applications, upstream support portion 142 is delivered within and/or via the same delivery tube as are tissue-engaging elements 144.

Typically, locking element 146 comprises a ratcheting element 158, comprising a plurality of ratchet teeth 160. Further typically, system 140 (e.g., prosthetic valve support 150 thereof) comprises a plurality of longitudinal guide members 162, each longitudinal guide member coupled to a respective tissue-engaging element, and each locking element 146 (e.g., ratcheting element 158) is coupled to and/or defined by a respective longitudinal guide member. Upstream support portion 142 is slidable along longitudinal guide members 162 (e.g., each longitudinal guide member is slidable through a respective hole 164 defined by the upstream support portion), typically by being pushed along the longitudinal guide members by one or more pushers 168 that are themselves typically slidable over the longitudinal guide members. Such sliding is typically facilitated by providing a counter force by simultaneous pulling on longitudinal guide members 162.

As shown in FIG. 5C, upstream support portion 142 typically comprises a plurality of receiving elements 166, disposed at a respective hole 164, and configured (1) to allow slidable passage of a respective longitudinal guide member 162 through the respective hole, and (2) to couple (e.g., lock) to a respective locking element 146. For example, each receiving element may comprise an eyelet, disposed around a respective hole, and configured to facilitate one-way movement therethrough of ratcheting element 158.

Coupling of upstream support portion 142 to tissue-engaging elements 144 thereby forms prosthetic valve support 150. Typically, tissue-engaging elements 144 are flexibly coupled to upstream support portion 142 (i.e., can move with respect to the upstream support portion while coupled to the upstream support portion). For example, longitudinal guide members 162 are typically flexible, and a portion of each flexible longitudinal guide member is disposed between a respective tissue-engaging element 144 (i.e., the point at which the longitudinal guide member is coupled to the tissue-engaging element) and upstream support portion 142 (i.e., the point at which the longitudinal guide member is coupled to the upstream support portion). Such coupling typically configures prosthetic valve support 150 to be couplable to native valve 10 without eliminating the valve function thereof, e.g., as described hereinabove. Upstream support portion 142 is typically annular, and shaped to define an opening therethrough, through which blood may flow.

Typically, a proximal portion of each longitudinal guide member 162 is decoupled from a distal portion of that longitudinal guide member and/or from the respective locking element 146, such as, but not limited to, by cutting. Such decoupling may be performed before introduction of prosthetic valve 148, as shown, or subsequently thereto.

Subsequently to coupling of upstream support portion 142 to tissue-engaging elements 144 (and thereby formation of prosthetic valve support 150), prosthetic valve 148 is delivered to native valve 10 and coupled to the tissue-engaging elements (e.g., to the prosthetic valve support) (FIG. 5D). Typically, prosthetic valve 148 comprises an expandable prosthetic valve, and is deployed (e.g., from a delivery tube 149) such that it (1) expands within the opening defined by upstream support portion 142 and/or the opening defined by stabilizing member 154, (2) applies a radially-expansive force against the upstream support portion and/or the stabilizing member, and (3) thereby becomes coupled thereto. For clarity, prosthetic valve 148 is shown in phantom outline.

Figure 7A:
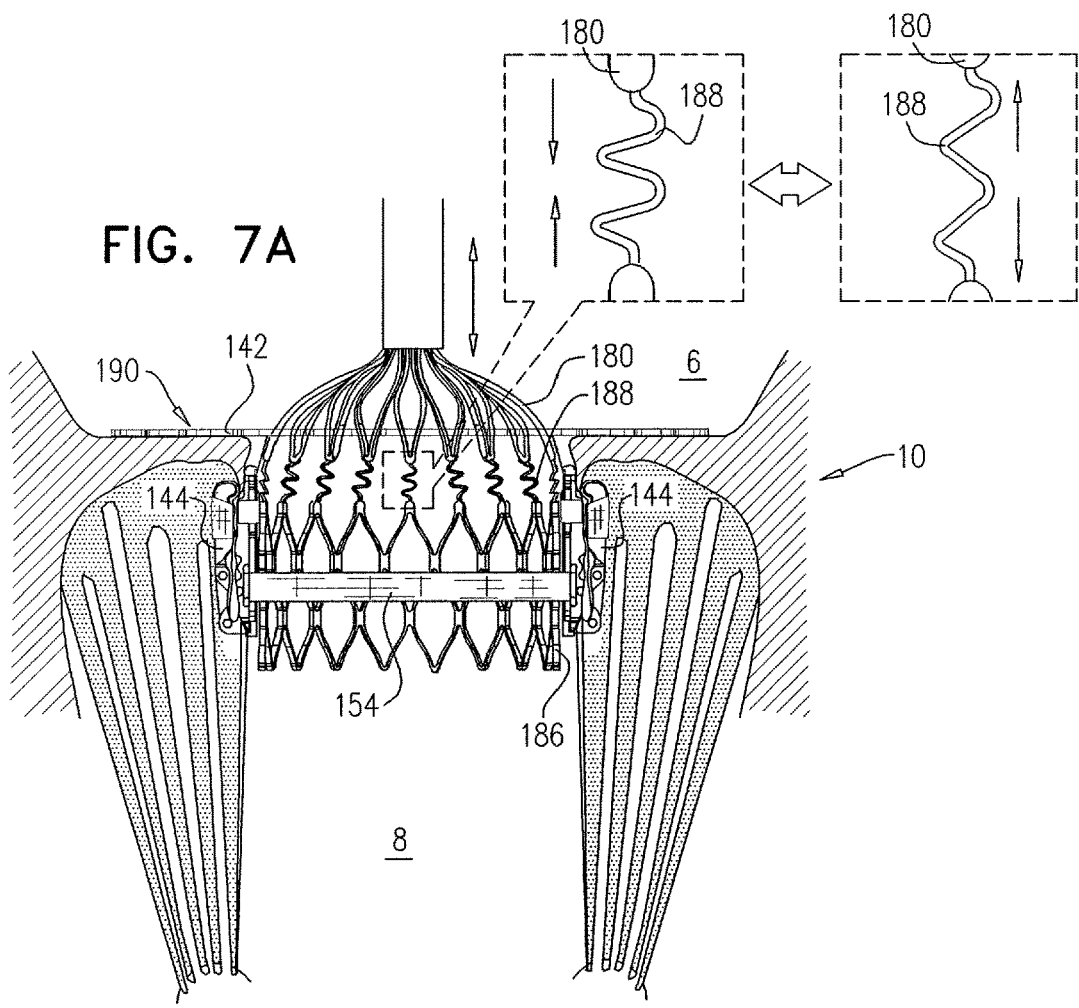
Figure 7B:
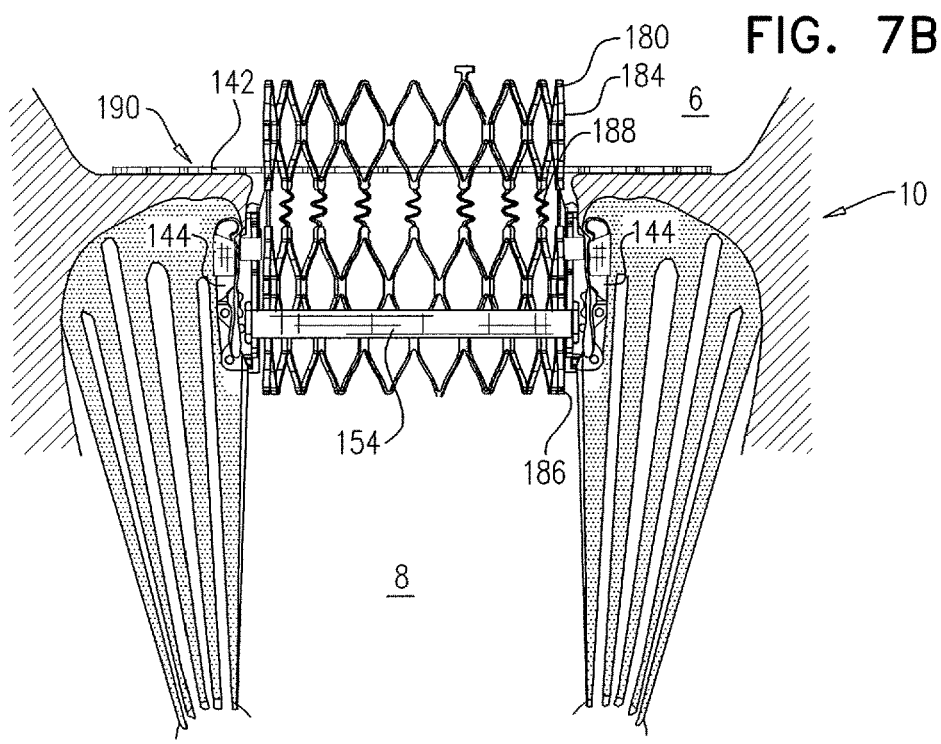

Reference is made to FIGS. 6 and 7A-B, which are schematic illustrations of a prosthetic valve 180 having a tubular valve body 182 that comprises an upstream portion 184, a downstream portion 186, and an elastic portion 188 disposed between the upstream portion and the downstream portion, in accordance with some applications of the invention. Prosthetic valve 180 is shaped to define a continuous lumen through portions 184, 188, and 186. Prosthetic valve 180 is configured to be implanted at native valve 10 such that an upstream portion 184 is disposed in an atrium 6 of the heart of the subject, and such that downstream portion 186 is disposed in a ventricle 8 of the heart of the subject. For example, prosthetic valve 180 may be coupled to a prosthetic valve support 190 that has previously coupled to the native valve. Prosthetic valve support 190 typically comprises tissue-engaging elements 144, upstream support portion 142, and stabilizing member 154, described hereinabove. For some applications, prosthetic valve support 190 comprises prosthetic valve support 150, described hereinabove. For some applications, prosthetic valve support 190 comprises a prosthetic valve support that comprises tissue-engaging elements 144, upstream support portion 142, and stabilizing member 156 that are provided pre-coupled to each other. For some applications, prosthetic valve support 190 may comprise another prosthetic valve support.

Tubular valve body 182 typically comprises a frame 192, such as a stent-like wire frame. As shown in FIG. 6, prosthetic valve 180 typically further comprises a covering 194, disposed over (e.g., covering) an inner surface of frame 192, thereby providing a sealed lumen from an upstream end to a downstream end of the tubular valve body. Typically, an excess of covering 194 is provided in the vicinity of elastic portion 188, so as to facilitate elastic stretching of the elastic portion.

Typically, prosthetic valve 180 comprises an expandable prosthetic valve, and is deployed such that it (1) expands within the opening defined by upstream support portion 142 and/or the opening defined by stabilizing member 154, (2) applies a radially-expansive force against the upstream support portion and/or the stabilizing member, and (3) thereby becomes coupled thereto. Typically, and as shown in FIGS. 7A-B, downstream portion 186 is expanded and coupled to stabilizing member 154 before upstream portion 184 is expanded and coupled to upstream support portion 142. While downstream portion 186 is coupled to member 154, and before upstream portion 184 is coupled to portion 142, elastic portion 188 may be stretched and compressed e.g., such as by moving upstream portion 184 further upstream and downstream. Such stretching and compressing changes a length of prosthetic valve 180, and for some applications, facilitates the coupling of a pre-determined portion of the prosthetic valve (e.g., of upstream portion 184) to upstream support portion 142, irrespective, to some degree, of (a) a distance between tissue-engaging elements 144 and upstream support portion 142, and/or (b) a dimension of native valve 10 (e.g., a length of leaflets 12). For some applications, such stretching and compressing adjusts a degree of tension of elastic portion 188, and may alternatively or additionally facilitate "tightening" of leaflets 12 against the implanted apparatus, such as drawing of the leaflets toward upstream support portion 142.

Figure 9:
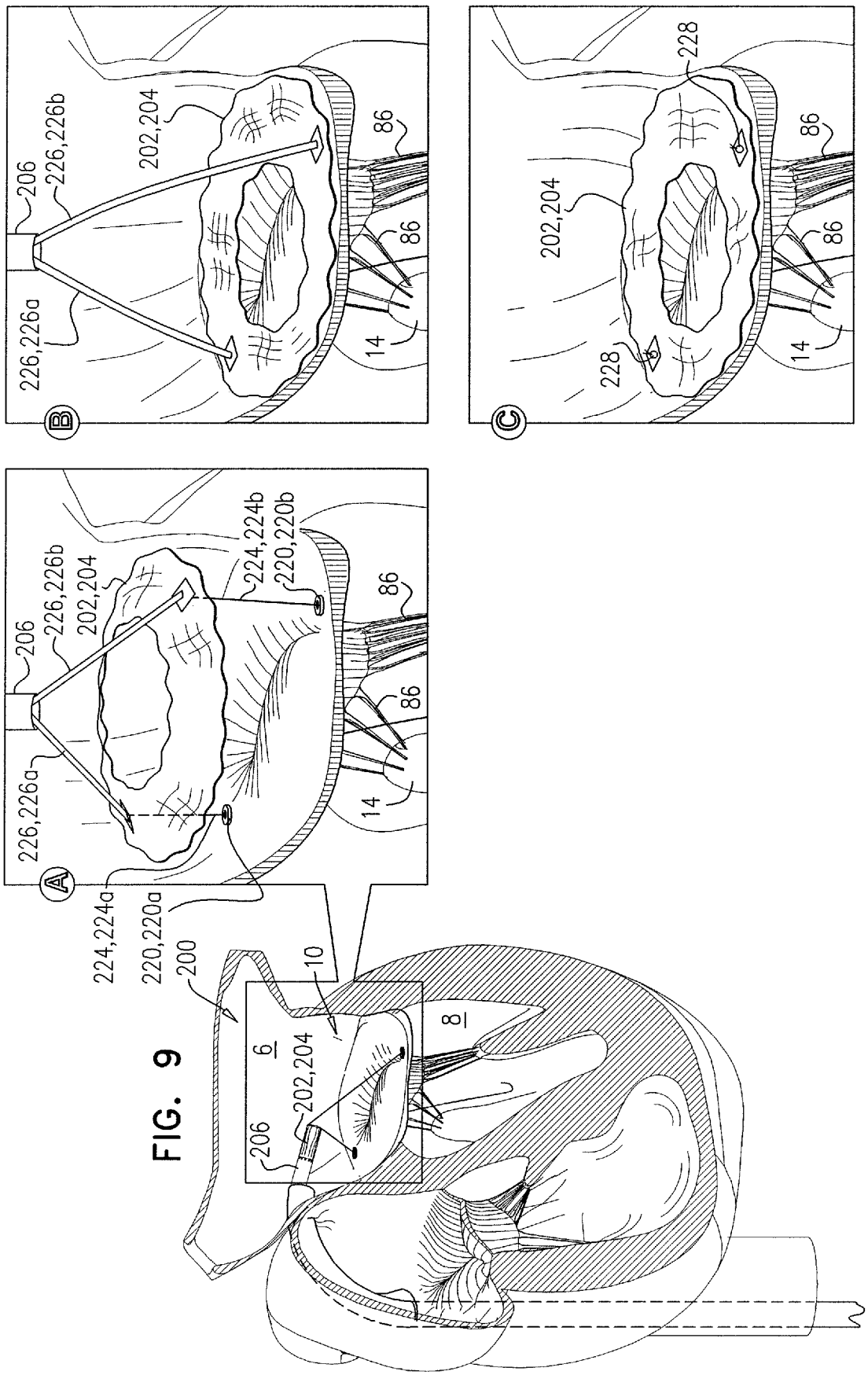
Figure 10:
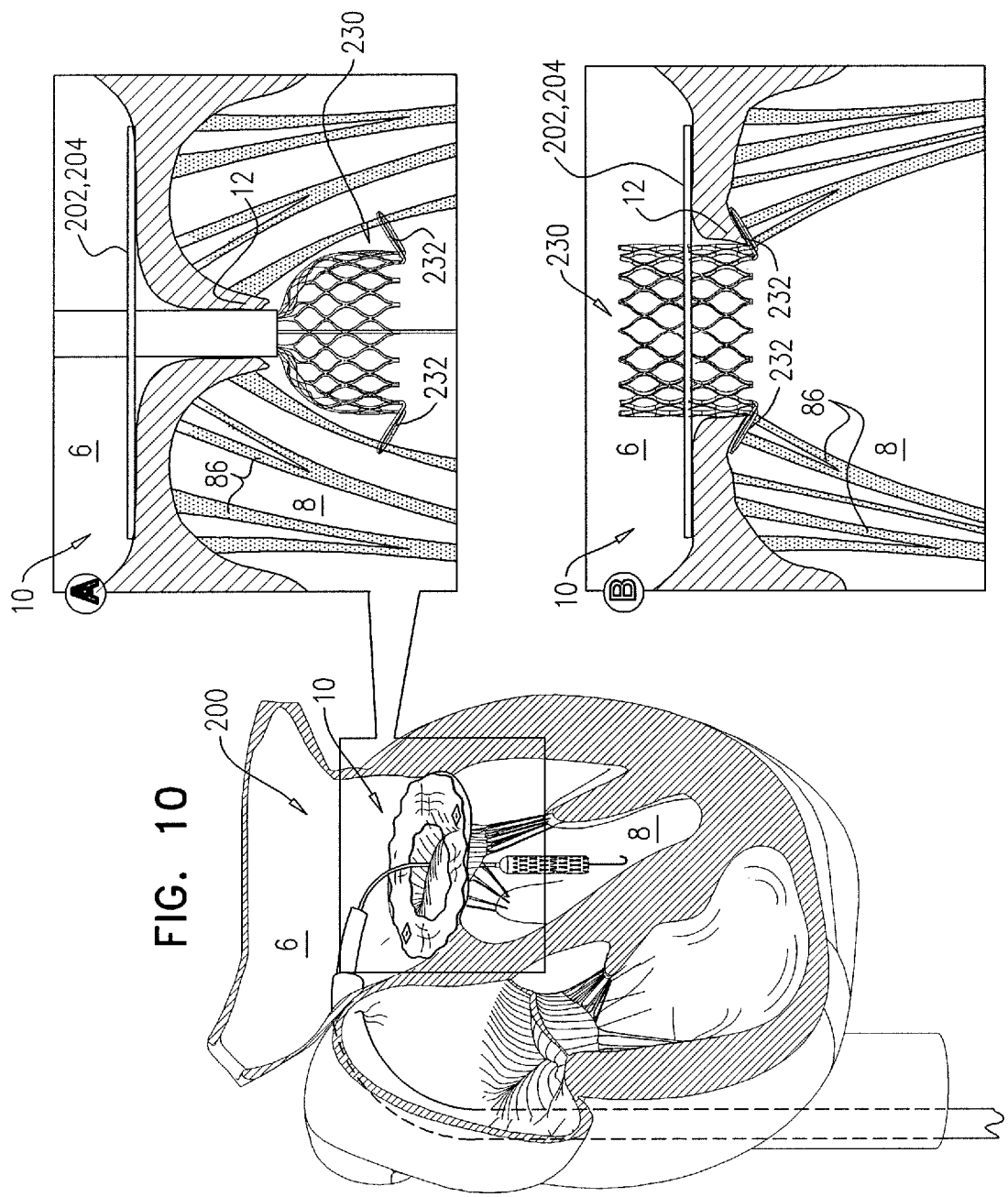

Reference is made to FIGS. 8-10, which are schematic illustrations of a system 200 for delivering and anchoring, to native valve 10, a prosthetic valve support 202 comprising an upstream support portion 204, in accordance with some applications of the invention. For some applications of the invention, prosthetic valve support 202 (and/or upstream support portion 204 thereof) comprises another prosthetic valve support described herein (and/or the upstream support portion thereof), such as prosthetic valve support 60 (and/or upstream support portion 62) or prosthetic valve support 150 (and/or upstream support portion 142).

Reference is now made to FIG. 8. System 200 comprises a delivery tube 206, which is shaped to define a lumen therethrough. A guidewire 208 protrudes from a lateral wall of delivery tube 206, such as from a hole 210 in the lateral wall. For some applications, tube 206 is shaped to define a secondary lumen that ends at hole 210, so as to provide guidewire 208 with a dedicated lumen. Guidewire 208 is advanced between leaflets 12 of native valve 10, such that the guidewire is disposed at a join of the leaflets, i.e., at a commissure 16 of the native valve (state A). Guidewire 208 is at least partly stiff, and provides resistance, which facilitates positioning of a distal end of tube 206. For example, guidewire 208 may bias the distal end to be disposed at a site in an arc around the commissure, the arc including part of the annulus and/or being in a vicinity of a fibrous trigone 17. For some applications, guidewire 208 is advanced between leaflets 12 and tube 206 is subsequently slid along (e.g., over) the guidewire. For some applications, tube 206 is advanced with guidewire 208.

A tissue anchor 220 (e.g., a first tissue anchor 220a) is advanced through at least a distal portion of tube 206, and is anchored to tissue of the native valve, such as tissue of the annulus of the native valve (state A). Typically, anchor 220 is advanced using an elongate anchor driver 222. For some applications, anchor 220 comprises a helical anchor, and is anchored to the tissue by being rotated using anchor driver 222.

Anchor driver 222 is reversibly coupled to anchor 220a, and is subsequently decoupled from the anchor and withdrawn proximally (e.g., withdrawn from the body of the subject) (state B). Anchor 220a is coupled to a longitudinal guide member 224 (e.g., a first guide member 224a), which is exposed from a lumen of anchor driver 222 when the driver is withdrawn (i.e., is slid proximally off of member 224). It is to be noted that at least a portion of guide member 224a remains disposed within tube 206. Tube 206 is moved toward a second commissure 14 of valve 10, and positioning of the tube is typically facilitated by guidewire 208 being disposed between leaflets 12 at the commissure, as described hereinabove.

A tissue anchor 220 (e.g., a second tissue anchor 220b) is advanced through at least a distal portion of tube 206, and is anchored to tissue of the native valve, such as tissue of the annulus of the native valve (state B). Typically, anchor 220b is advanced using an elongate anchor driver, such as the same anchor driver 222, or a second anchor driver. It is to be noted that anchor 220 and anchor driver 222 are advanced through tube 206 while at least a portion of first guide member 224a is disposed within tube 206 (i.e., advanced past at least a portion of member 224a).

Anchor driver 222 is subsequently decoupled from anchor 220b and is withdrawn proximally (e.g., withdrawn from the body of the subject) (state C). Anchor 220b is coupled to a longitudinal guide member 224 (e.g., a second guide member 224b), which is exposed from the lumen of anchor driver 222 when the driver is withdrawn. Native valve is thereby left with respective distal ends of two guide members 224 coupled thereto (e.g., coupled to the annulus thereof)(state D).

Reference is now made to FIG. 9. Prosthetic valve support 202 (e.g., upstream support portion 204 thereof) is advanced along (e.g., slid over) guide members 224 (e.g., guide members 224a and 224b) (state A). Typically, support 202 is advanced through delivery tube 206 in a compressed configuration (e.g., a generally cylindrical configuration), and automatically expands into an expanded configuration (e.g., a generally annular configuration) when deployed from the distal end of tube 206. Typically, support 202 is pushed through delivery tube 206 and against the upstream (e.g., atrial) surface of valve 10 using one or more control tubes 226 (e.g., a first control tube 226a and a second control tube 226b). Prosthetic valve support 202 (e.g., upstream support portion 204 thereof) is shaped to define one or more (e.g., two) holes, through which a respective guide member 224 is slidable. Control tubes 226 are shaped to define a lumen through which a respective guide member 224 is slidable, and typically have a transverse width (e.g., a diameter) that is greater than a diameter of the holes in prosthetic valve support 202. Thereby when control tubes 226 are slid distally over guide members 224, they push prosthetic valve support 202 distally (states A and B).

Subsequently, prosthetic valve support 202 is anchored to native valve 10 by inhibiting movement of the prosthetic valve support with respect to guide members 224. For example, a stopper 228 may be slid along each guide member and fastened to the guide member in the vicinity of the prosthetic valve support. For some applications, each guide member 224 comprises two discrete filaments, each filament being slidable through a separate hole in the prosthetic valve support, and the prosthetic valve support is anchored by tying the filaments together, optionally facilitated by a pledget (not shown). Typically, a proximal portion of each guide member is subsequently removed, such as by decoupling that portion from a distal portion, e.g., by cutting.

Reference is now made to FIG. 10. Subsequently, a prosthetic valve 230 is implanted at native valve 10 by being deployed at, and coupled to, prosthetic valve support 202, e.g., as described hereinabove for prosthetic valve 148 with reference to FIG. 5D, mutatis mutandis. For some applications, prosthetic valve 230 comprises tissue-engaging elements 232, such as anchors and/or clips, which facilitate implantation of the prosthetic valve by coupling to leaflets 12 of valve 10. For some such applications, and as shown with reference to FIG. 10, prosthetic valve 148 is partially deployed (state A), and then withdrawn proximally before being fully deployed (state B), so as to sandwich leaflets 12 against prosthetic valve support 202 (e.g., upstream support portion 204 thereof).

Reference is again made to FIGS. 8-10. Typically, each anchor 220 fits snugly through delivery tube 206. Typically, first guide member 224a is sufficiently thin to allow second anchor 220b to snugly fit through the delivery tube and past member 224a. For some applications, anchor driver 222 also fits snugly through delivery tube 206 and/or past member 224a. For example, guide member 224a may have a transverse cross-sectional area that is less than half (e.g., less than 25%, such as less than 10%) of a cross-sectional area of anchor 200 and/or anchor driver 222. For some applications, prosthetic valve support 202 (e.g., upstream support portion 204 thereof), in the compressed configuration thereof, fits snugly through delivery tube 206 and/or past guide members 224. For some applications, prosthetic valve 230, in a compressed configuration thereof, fits snugly through delivery tube 206.

For some applications, anchor 200, prosthetic valve support 202 in the compressed configuration thereof, and prosthetic valve 230 in the compressed configuration thereof, have respective transverse cross-sectional areas that are generally the same as each other (e.g., having a difference of less than 50%, such as less than 30%, such as less than 10%). For example, prosthetic valve support in the compressed configuration is typically less than 50% (e.g., less than 30%, such as less than 10%) wider than each anchor 200. For some such applications, this provides an efficient use of space within delivery tube 206, and thereby allows the use of a narrow delivery tube, e.g., because none of the anchor, support, or valve are more than 50% wider than another. In contrast, for some applications in which two or more anchors and/or anchor drivers are delivered in parallel, a delivery tube would have to be significantly wider than (e.g., twice as wide as) the delivery tube of system 200.

Figure 11A:
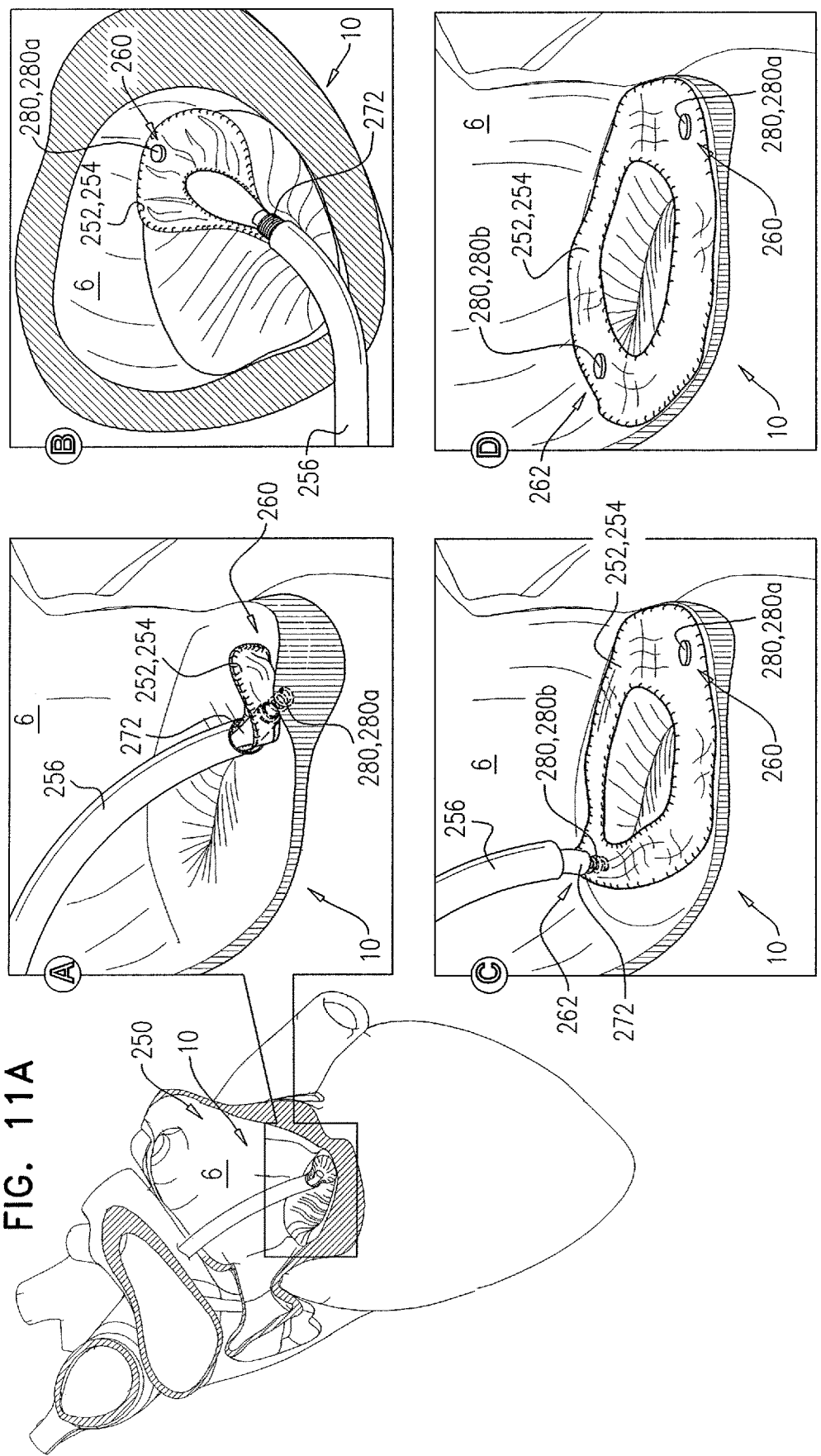

Reference is made to FIGS. 11A-C, which are schematic illustrations of a system 250 for delivering and anchoring to native valve 10, a prosthetic valve support 252 comprising an upstream support portion 254, in accordance with some applications of the invention. Prosthetic valve support 252 is delivered, via a delivery tube 256, to native valve 10 in a delivery configuration in which the prosthetic valve support (e.g., upstream support portion 254 thereof) assumes a shape that generally defines a channel (e.g., a lumen) therethrough, such as a generally tubular (e.g., cylindrical) shape. For example, upstream support portion 254 typically has expanded working configuration in which it is generally annular (FIG. 11A state D), and is "rolled" into the delivery configuration (e.g., into a generally tubular shape).

FIGS. 11B-C show upstream support portion 254 in the delivery configuration thereof, in accordance with respective applications of the invention. In both FIG. 11B and FIG. 11C, state A shows the upstream support portion in the annular expanded configuration, and state B shows the upstream support portion in the tubular delivery configuration. FIG. 11B shows an application in which upstream support portion 254 comprises an upstream support portion 254' which, in the annular expanded configuration thereof, has an outer diameter d1' and an inner diameter d2'. FIG. 11C shows an application in which upstream support portion 254 comprises an upstream support portion 254" which, in the annular expanded configuration thereof, has an outer diameter d1" and an inner diameter d2". Upstream support portions 254' and 254" are typically identical except that inner diameter d2' is smaller with respect to outer diameter d1', than is inner diameter d2" with respect to outer diameter d1", and therefore upstream support portion 254' has a greater surface area than does upstream support portion 254".

State B of FIGS. 11B-C show upstream support portions 254' and 254" in their respective delivery configurations. Upstream support portion 254' defines a generally continuous tubular shape having a distal end 260, a proximal end 262, and a generally continuous, uninterrupted channel 255' therebetween along a central longitudinal axis 258 defined by the upstream support portion. Due to its greater relative inner diameter, upstream support portion 254" defines a tubular shape in which a channel 255" between distal end 260 and proximal end 262 is interrupted and/or incomplete. FIG. 11C shows an example in which upstream support portion 254" defines a distal tubular region 261, a proximal tubular region 263, and at least one interruption 265 therebetween. That is, at at least one part of the upstream support portion, compared to an uninterrupted tube, at least one portion of the lateral wall of the tube is absent. Nevertheless, upstream support portion 254", in the delivery configuration thereof, also defines a channel 255" therethrough.

The upstream support portion configurations in FIGS. 11B and 11C are intended to illustrate different applications in which the upstream support portion, in the delivery configuration thereof, defines a channel. These figures are not intended to limit the scope of the invention to these particular applications. For example, the scope of the invention includes, inter alia, as shown in state C of FIG. 11B, a delivery configuration in which only opposing edges of the upstream support portion touch, such that few, if any, portions of the lateral wall of the tubular shape completely circumscribe a given longitudinal site of the tubular shape. Nevertheless, the upstream support portion, in this delivery configuration, also defines a channel therethrough.

Upstream support portion 254 has a tissue-contacting side 274, configured to be placed against the atrial surface of valve 10 (e.g., against the annulus of the valve), and an opposing side 276, and defines an opening 278 therebetween. It is to be noted that, in the delivery configuration, opposing side 276 is disposed closer to central longitudinal axis 258 than is tissue-contacting side 274.

Reference is again made to FIG. 11A. Distal portion 260 of upstream support portion 254 is anchored to a first site of the annulus of the native valve using a tissue-engaging element, such as a tissue anchor 280 (e.g., a first tissue anchor 280a) (state A). Typically, anchor 280 is driven through upstream support portion 254 and into the tissue using an anchor driver 272, which is disposed within delivery tube 256. Typically, anchor driver 272 is slidable through the channel defined by the generally tubular shape of the upstream support portion, and is configured to move anchor 280a through at least part of that channel. For some applications, anchor 280 comprises a helical tissue anchor, and is anchored by being rotated by anchor driver 272. Anchor 280 may alternatively comprise a different type of tissue anchor, such as a harpoon-like tissue anchor.

Typically, distal portion 260 is anchored by (1) exposing the distal portion from delivery tube 256 and pressing it against the tissue of the annulus such that it deflects (e.g., bends) back and is disposed generally in front of the channel defined by the remainder of the upstream support portion that is disposed in the delivery configuration within tube 256, and (2) advancing anchor 280 distally through the upstream support portion (i.e., through distal portion 260 thereof) and into the tissue. For some applications, a plane defined by the distal portion is disposed at greater than 45 degrees with respect to longitudinal axis 258.

For some applications, during transluminal advancement, anchor 280a is disposed proximally to upstream support portion 254 (e.g., within a proximal portion of the delivery tube, or outside of the body of the subject), and driver 272 subsequently moves the anchor from a proximal end of the channel defined by the upstream support portion, through the channel. That is, driver 272 may slide anchor 280a past at least part of the longitudinal axis of upstream support portion 254 (e.g., past most of the longitudinal axis of the upstream support portion, such as past at least 80 percent of the longitudinal axis of the upstream support portion). Alternatively, during transluminal advancement, anchor 280a and a distal portion of anchor driver 272 may be already disposed within the channel defined by the upstream support portion, and the driver subsequently moves anchor 280a only slightly distally so as to drive the anchor through distal portion 260 and into the tissue. For some such applications, the delivery tube is transluminally advanced while the upstream support portion is disposed within a distal portion of the delivery tube, and the tissue anchor and the distal portion of the anchor driver are disposed within the channel.

Subsequently, upstream support portion 254 is further exposed from delivery tube 256 (e.g., by withdrawing the delivery tube proximally), and the distal end of the delivery tube is moved toward a second site of the annulus (state B). As upstream support portion 254 is progressively exposed from delivery tube 256, the upstream support portion typically progressively transitions (e.g., expands and/or unrolls) automatically toward the working configuration thereof. To facilitate such automatic transition toward the working configuration, upstream support portion 254 may comprise a frame (e.g., comprising a shape-memory material such as nitinol), which may be covered in a covering, such as a fabric.

Subsequently, a proximal portion 262 of upstream support portion 254 is anchored to the second site using a tissue anchor 280 (e.g., a second tissue anchor 280b) in a similar manner to that described for distal portion 260 (state C). Typically, during anchoring of proximal portion 262, the proximal portion is held near the distal end of delivery tube 256 by a deployment tool (e.g., slightly inside the delivery tube or just outside of the delivery tube). The deployment tool is not visible in state C; it is obscured by anchor driver 272. Following anchoring, proximal portion 262 is released by the deployment tool, and delivery tube 256 and driver 272 are withdrawn (state D).

It is to be noted that when prosthetic valve support 252 is disposed within delivery tube 256, the delivery tube and the prosthetic valve support (e.g., upstream support portion 254 thereof) share a common central longitudinal axis (e.g., are coaxial) (e.g., axis 258; FIGS. 11B-C), and that system 250 facilitates the driving of anchors through the prosthetic valve support by deflecting the portion of the prosthetic valve support that is to be anchored to intersect with the longitudinal axis, such that anchoring is possible by movement of the anchors (and anchor driver 272) along the longitudinal axis.

Prosthetic valve support 252 is typically subsequently used to facilitate implantation of a prosthetic valve, such as a prosthetic valve described hereinabove, or another prosthetic valve, e.g., by the prosthetic valve being expanded within the opening defined by the prosthetic valve support. Reference is again made to FIGS. 1A-11C. Typically, the techniques described hereinabove are performed transluminally (e.g., transfemorally). For some applications, the techniques are performed intercostally. It is therefore to be noted that the orientations and positions of the apparatus shown hereinabove with respect to atrium 6 of the subject are for clarity, and are not intended to limit the invention to a particular route to the atrium. Similarly, for some applications, the techniques described hereinabove are performed transapically, and thereby apparatus is delivered to the native valve via left ventricle 8 of the subject. It is to be further noted that, although native valve 10 is shown hereinabove as the mitral valve of the subject, the techniques described hereinabove may be used on other heart valves of the subject, such as the tricuspid valve, mutatis mutandis.

Reference is again made to FIGS. 1A-11C. For some applications, the prosthetic valve support is implanted (e.g., coupled to the native valve) without eliminating native functioning of the native leaflets. Thereby, for such applications, the prosthetic valve support (and for some such applications, the prosthetic valve) may be implanted without the use of cardiopulmonary bypass. For example:

Tissue-engaging elements 24 (FIGS. 1A-C) and 144 (FIGS. 5A-D) are typically configured to move with the movement of the native leaflets (e.g., by deflecting with respect to the respective upstream support portion).

Prosthetic valve support 202 (FIGS. 8-10) and 252 (FIG. 11) are typically anchored to the annulus of the native valve without contacting the native leaflets.

Reference is again made to FIGS. 1A-11C. For some applications, a separate prosthetic valve support is not used, but rather the upstream support portion is integral with the prosthetic valve (e.g., is coupled to the upstream end of the generally tubular valve body).

Reference is again made to FIGS. 1A-11C. It is to be noted that elements and/or techniques described herein with reference to a particular figure may be combined and/or substituted with elements and/or techniques described herein with reference to one or more other figures, mutatis mutandis. In particular, for some applications, elements of apparatus described herein are interchangeable with other elements that have the same name, mutatis mutandis. For example:

For some applications, prosthetic valve 148 comprises, or may be substituted with, prosthetic valve 102, prosthetic valve 180, or prosthetic valve 230, mutatis mutandis.

For some applications, upstream support portion 142 comprises, or may be substituted with, upstream support portion 62, upstream support portion 204, or upstream support portion 254, mutatis mutandis.

For some applications, tissue-engaging element 232 comprises, or may be substituted with, tissue-engaging element 24 or tissue-engaging element 144, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a prosthetic valve at a native valve of a heart of a subject, the apparatus comprising:
   a delivery tube, transluminally advanceable to the heart of the subject; and
   a prosthetic valve support, configured to support the prosthetic valve at the native valve, and defining an upstream support portion, the upstream support portion being a generally annular disc, and:
      having a working configuration in which the upstream support portion is a generally annular disc that has (1) a tissue-contacting side configured to be placed against an atrial surface of the native valve, and (2) an opposing side, and defines an opening therebetween,
      having a delivery configuration in which the upstream support portion is rolled up to create a channel having a central longitudinal axis, and is disposed within the delivery tube, and
      being configured to be transitioned from the delivery configuration to the working configuration by being exposed from the delivery tube, and unrolled.

2. The apparatus according to claim 1, wherein, in the delivery configuration, the upstream support portion has a distal portion and a proximal portion, and shapes the channel to be an uninterrupted lumen between the distal portion and the proximal portion.

3. The apparatus according to claim 1, wherein the delivery tube is configured to retain the upstream support portion in the delivery configuration, and the upstream support portion is configured to automatically transition toward the working configuration by automatically unrolling upon becoming exposed from the delivery tube.

4. The apparatus according to claim 1, wherein, while the upstream support portion is in the delivery configuration, at any given part of the upstream support portion, the opposing side of the upstream support portion is disposed closer to the central longitudinal axis than is the tissue-contacting side.

5. The apparatus according to claim 1, wherein, while the upstream support portion is in the delivery configuration, the central longitudinal axis of the channel is collinear with a central longitudinal axis of the delivery tube.

6. A method for use with a prosthetic valve at a native valve of a heart of a subject, comprising:

transluminally advancing, to a heart valve of the subject, a prosthetic valve support that defines an upstream support portion, the advancing being while the upstream support portion is in a delivery configuration in which the upstream support portion (i) is rolled up to create a channel having a central longitudinal axis, and (ii) is disposed within a delivery tube;

subsequently, facilitating transition of the upstream support portion into a working configuration by exposing the upstream support portion from the delivery tube and facilitating unrolling of the upstream support portion, the working configuration being a configuration in which:

the upstream support portion is a generally annular disc that has (1) a tissue-contacting side, and (2) an opposing side, the upstream support portion defines an opening between the tissue-contacting side and the opposing side, and the tissue-contacting side is disposed against an atrial surface of the native valve; and using the prosthetic valve support, supporting the prosthetic valve at the native valve.

7. The method according to claim 6, wherein facilitating transition of the upstream support portion into the working configuration comprises exposing the upstream support portion from the delivery tube such that the upstream support portion automatically unrolls.

8. The method according to claim 6, wherein, in the delivery configuration, the upstream support portion has a proximal portion and a distal portion, the channel being defined between the proximal portion and the distal portion, and wherein the method further comprises pressing the distal portion against the annulus such that the distal portion deflects with respect to the delivery tube.

9. The method according to claim 6, wherein, in the delivery configuration, the upstream support portion has a proximal portion and a distal portion, the channel being defined between the proximal portion and the distal portion, and wherein the method further comprises pressing the distal portion against the annulus such that the distal portion deflects with respect to the proximal portion.

* * * * *